(12) United States Patent
Tajima

(10) Patent No.: US 10,626,440 B2
(45) Date of Patent: Apr. 21, 2020

(54) SEQUENCER PRETREATMENT DEVICE AND METHOD THEREOF

(71) Applicant: Universal Bio Research Co., Ltd., Chiba (JP)

(72) Inventor: Hideji Tajima, Matsudo (JP)

(73) Assignee: UNIVERSAL BIO RESEARCH CO., LTD. (JP)

(*) Notice: Subject to any disclaimer, the term of this patent is extended or adjusted under 35 U.S.C. 154(b) by 362 days.

(21) Appl. No.: 14/892,398

(22) PCT Filed: May 21, 2014

(86) PCT No.: PCT/JP2014/063498
§ 371 (c)(1),
(2) Date: Nov. 19, 2015

(87) PCT Pub. No.: WO2014/189085
PCT Pub. Date: Nov. 27, 2014

(65) Prior Publication Data
US 2016/0122801 A1    May 5, 2016

(30) Foreign Application Priority Data

May 21, 2013   (JP) ................................ 2013-107514

(51) Int. Cl.
*C12Q 1/6806*    (2018.01)
*B01L 7/00*    (2006.01)
(Continued)

(52) U.S. Cl.
CPC ........ *C12Q 1/6806* (2013.01); *B01J 19/0046* (2013.01); *B01L 7/52* (2013.01);
(Continued)

(58) Field of Classification Search
CPC .......... B01J 19/0046; B01J 2219/00313; B01J 2219/00328; B01J 2219/0036;
(Continued)

(56) References Cited

U.S. PATENT DOCUMENTS 4,683,202 A   7/1987   Mullis
5,958,349 A   9/1999   Petersen et al.
(Continued)

FOREIGN PATENT DOCUMENTS

JP   8-320274    3/1996
JP   2622327     6/1997
(Continued)

OTHER PUBLICATIONS

International Search Report (including English Translation) and Written Opinion received in Patent Cooperation Treaty Application No. PCT/JP2014/063498, dated Aug. 19, 2014.
(Continued)

*Primary Examiner* — Teresa E Strzelecka
(74) *Attorney, Agent, or Firm* — Andrus Intellectual Property Law, LLP

(57) ABSTRACT

A sequencer pretreatment device includes a suction and discharge mechanism, a nozzle head having a nozzle for mounting a dispensing tip, a container group for accommodating liquids including magnetic particle suspension, a moving mechanism for causing relative movement between the nozzle and the container group, and a magnetic unit that exerts a magnetic field to the mounted dispensing tip. A method includes an extraction step of mixing a sample, extraction reagent solution, and magnetic particle suspension in the container group and extracting nucleic acid, a fragmentation producing step of fragmentating the nucleic acid by mixing with fragmentation solution accommodated in the container group and producing a fragment of a base (Continued)

sequence having a molecular weight corresponding to a sequencer using magnetic particle suspension using the sequencer pretreatment device, and an amplification pretreatment step of dispensing a solution containing the fragment into the reaction vessel using the sequencer pretreatment device.

18 Claims, 8 Drawing Sheets

(51) Int. Cl.
| | |
|---|---|
| *B01J 19/00* | (2006.01) |
| *G01N 35/00* | (2006.01) |
| *G01N 35/10* | (2006.01) |
| *C12N 15/10* | (2006.01) |
| *B01L 3/00* | (2006.01) |
| *B01L 3/02* | (2006.01) |
| *C12Q 1/6844* | (2018.01) |

(52) U.S. Cl.
CPC ..... *C12N 15/1013* (2013.01); *G01N 35/0098* (2013.01); *G01N 35/1065* (2013.01); *B01J 2219/0036* (2013.01); *B01J 2219/00313* (2013.01); *B01J 2219/00328* (2013.01); *B01J 2219/00369* (2013.01); *B01J 2219/00371* (2013.01); *B01J 2219/00466* (2013.01); *B01J 2219/00468* (2013.01); *B01J 2219/00479* (2013.01); *B01J 2219/00495* (2013.01); *B01J 2219/00596* (2013.01); *B01J 2219/00693* (2013.01); *B01J 2219/00722* (2013.01); *B01L 3/0268* (2013.01); *B01L 3/50855* (2013.01); *B01L 2300/0829* (2013.01); *B01L 2400/0421* (2013.01)

(58) Field of Classification Search
CPC .... B01J 2219/00369; B01J 2219/00371; B01J 2219/00466; B01J 2219/00468; B01J 2219/00479; B01J 2219/00495; B01J 2219/00596; B01J 2219/00693; B01J 2219/00722; B01L 2300/0829; B01L 2400/0421; B01L 3/50855; B01L 7/52; B01L 3/0268; C12N 15/1013; C12Q 1/6806; G01N 35/0098; G01N 35/1065
See application file for complete search history.

(56) References Cited

U.S. PATENT DOCUMENTS

| | | |
|---|---|---|
| 6,455,325 B1 | 9/2002 | Tajima |
| 2006/0205064 A1 | 9/2006 | Tajima |
| 2015/0315630 A1 | 11/2015 | Tajima |

FOREIGN PATENT DOCUMENTS

| | | |
|---|---|---|
| JP | 2000511435 A | 9/2000 |
| JP | 2002010777 A | 1/2002 |
| WO | WO 97/46712 A2 | 12/1997 |
| WO | WO 01/11364 A1 | 2/2001 |
| WO | WO 2012/050198 A1 | 4/2012 |

OTHER PUBLICATIONS

International Preliminary Report on Patentability (including English Translation) received in Patent Cooperation Treaty Application No. PCT/JP2014/063498, dated Nov. 21, 2015.
Akutsu, Jun-ichi, et al, "Development of an Integrated Automation System with a Magnetic Bead-Mediated Nucleic Acid Purification Device for Genetic Analysis and Gene Manipulation," Biotechnology and Bioengineering, vol. 86, No. 6, Jun. 20, 2004, pp. 667-671.
Nishioka, Junji, et al., "DNA Chushutsu-ho no Hyoka to Hyojunka," Japanese Journal of Clinical Chemistry, vol. 37, Suppl. 1, Aug. 29, 2008, pp. 43-45.

SEQUENCER PRETREATMENT DEVICE AND METHOD THEREOF

CROSS REFERENCE

This application is a United States national phase application of co-pending international patent application number PCT/JP2014/063498, filed May 21, 2014, which claims priority to Japanese patent application number 2013-107514, filed May 21, 2013, the entire disclosures of which are hereby incorporated herein by reference.

TECHNICAL FIELD

The present invention relates to a sequencer pretreatment device and a method thereof.

BACKGROUND ART

Conventionally, capillary sequencing by the dideoxy method has been often used in order to determine base sequence of nucleic acid (DNA, RNA, etc.) or a fragment thereof (oligonucleotide, nucleotide, etc.). In this method, four normal DNA synthesis systems are prepared, to which chain terminating nucleotide (terminator) of a low concentration is added to cause a reaction therewith. As the terminator, only one type out of four types of dideoxynucleotides (ddATP, ddGTP, ddCTP, and ddTTP) is used. DNA polymerase continues to synthesize DNA while incorporating deoxyribonucleotide corresponding to a template sequence. However, the reaction sometimes stops upon incorporation of the corresponding terminator. As a result, DNA fragments of various lengths corresponding to a base of the terminator are obtained. For example, in a system where ddATP is added as the terminator, a 3' end base of a resulting DNA fragment is adenine. This allow a sequence to be properly determined only with the four reaction systems without requiring simple DNA synthesis to be performed first. In this method, although a high accuracy is obtained, throughput such as the number of analyses that can be obtained in one performance of analysis is limited.

Currently, a significant improvement has been made in analysis throughput of sequencing. DNA sequencers capable of analyzing DNA or a fragment thereof having a large-scale base sequence of mega or giga order have been implemented (Illumina Inc. and Roche).

In this method, the extracted nucleic acid or a fragment thereof, which is a target of base sequence determination, is required to be fragmentated into base sequence of a substantially uniform size having a predetermined number of bases (e.g. approximately several tens to 1000 b). Furthermore, it is a prerequisite that the fragmentated pieces having a large number of bases are accommodated in a reaction vessel together with various reagents, a primer, DNA polymerase, nucleotide, and reaction buffer or the like with the nucleic acid functioning as a template DNA for performing amplification under controlled temperature.

However, when performing analysis of such a large number of base sequences, the target nucleic acid has to be amplified with a high accuracy. In particular, there may be cases where an erroneous conclusion is led by amplification where nucleic acid other than the target nucleic acid is mixed, or repeating processing many times from the beginning to the amplification after performing the amplification processing. In order to analyze base sequence of target nucleic acid, uniform fragmentation of nucleic acid or a fragment thereof into a predetermined number of base sequences is required for successful analysis of large-scale base sequences.

Therefore, to see whether the target nucleic acid or a fragment thereof having been extracted, fragmentated, and further amplified meets the treatment purpose, a portion is extracted manually from the nucleic acid or fragment thereof having been extracted and fragmentated and labeled with fluorescence or the like to monitor a size of molecular weight by electrophoresis. This is time to consuming as well as posing a risk of cross contamination. Moreover, performing the electrophoresis requires a high degree of technique, thus presently requiring a researcher or technician specialized in nucleic acid. Therefore, a doctor or the like not specialized in this field cannot easily use the technique in clinical application.

The above prevents generalization of genetic analysis or expansion of clinical application in hospitals using a large-scale sequencer. Therefore, it is important to provide accurate pretreatment where cross contamination is prevented and labor of a user is reduced in clinical use while allowing for the amplification process suitable for a large-scale sequencer and performing reliable amplification of nucleic acid with a high accuracy. Furthermore, full automation is required where extraction of nucleic acid to amplification and further to measurement is consistently automated. It is also important to downsize a device and to provide a high-accuracy device at a low cost.

CITATION LIST

Patent Literature

Patent Literature 1 JP 2622327 B
Patent Literature 2 JP 2000 to 511435 W
Patent Literature 3 U.S. Pat. No. 5,958,349
Patent Literature 4 JP 2002 to 10777 A

SUMMARY OF INVENTION

Technical Problem

The present invention has been made to solve the above problems. A first object is to provide a sequencer pretreatment device and a method thereof whereby at least extraction of nucleic acid or a fragment thereof to amplification pretreatment is consistently automated as pretreatment for a sequencer capable of reading large-scale base sequence of the nucleic acid or a fragment thereof including a number of bases, and thus capable of performing speedy and efficient processing without requiring user intervention.

A second object is to provide a sequencer pretreatment device and a method thereof whereby pretreatment for a sequencer including at least extraction of nucleic acid is made possible to be consistently performed not in a manual manner, thereby allowing a foreign matter to be prevented from entering, namely, contamination, and providing a reliable product with high quality.

A third object is to provide a sequencer pretreatment device and a method thereof where, by incorporating a dispenser in the device, a scale of the device is not increased and thus can be manufactured and used at a reasonable cost.

Solution to Problem

A first aspect of the invention is a sequencer pretreatment method using a sequencer pretreatment device including: a suction and discharge mechanism for sucking and discharging gas; a nozzle head having one or more nozzles for detachably mounting one or more dispensing tips communicated with the suction and discharge mechanism and capable of sucking and discharging liquid; a container group including at least a reaction vessel and a liquid accommodating portion for accommodating various liquids including magnetic particle suspension; a moving mechanism for causing the nozzle relative movement with respect to the container group; and a magnetic unit capable of exerting a magnetic field to the inside of the dispensing tip mounted to the nozzle. The method includes: an extraction step of mixing a sample, extraction reagent solution, and magnetic particle suspension accommodated in the container group and extracting nucleic acid from the sample; a fragmentation producing step of fragmentating the extracted nucleic acid by mixing with fragmentation solution accommodated in the container group and producing, from the fragmentated nucleic acid, a fragment of a base sequence having the number of bases within a predetermined range corresponding to a sequencer using the magnetic particle suspension using the sequencer pretreatment device; and an amplification pretreatment step of dispensing a predetermined volume of solution containing the produced fragment into the reaction vessel together with amplification solution using the sequencer pretreatment device.

Here, the container group is normally provided on a stage and preferably provided with the reaction vessel, a plurality of liquid accommodating portions for accommodating liquids such as a sample and reagent, and the dispensing tip as well as a tip accommodating portion for accommodating a tip such as perforating tip for perforating a film provided so as to cover an opening of the container group. Also, the container group includes a microplate where wells, which are the plurality of liquid accommodating portions, are aligned in a matrix or column (row) shape and a cartridge-shaped container where wells, which are the plurality of liquid accommodating portions, are aligned in a column shape.

Specifically, the container group preferably includes at least one or more liquid accommodating portions for accommodating a sample, one or more liquid accommodating portions for accommodating extraction reagent solution for extracting nucleic acid from the sample, one or more liquid accommodating portions for accommodating the fragmentation solution, one or more liquid accommodating portions for accommodating magnetic particle suspension suspending magnetic particles capable of binding with respective nucleic acid or fragments thereof, one or more liquid accommodating portions for accommodating binding promoter solution for promoting binding between the nucleic acid or fragments thereof and magnetic particles, one or more liquid accommodating portions for accommodating dissociation solution causing dissociation between the nucleic acid or fragments thereof and magnetic particles bound with each other, one or more liquid accommodating portions for accommodating the amplification solution, one or more reaction vessels temperature of which is controllable, and one or more tip accommodating portions for detachably accommodating or holding one or more dispensing tips in the nozzles. Furthermore, an amplification step is required when amplification is also required as sequencer pretreatment and one or more liquid accommodating portions for accommodating electrophoresis solution are required when acceptability of a molecular weight is determined. The electrophoresis solution will be described later.

The "magnetic particle suspension" is liquid where magnetic particles, processed such that nucleic acid or fragment thereof is captured thereby, are suspended therein and includes, for example, silica, glass, and those coated with a porous material such as a fiber material when a target is captured by physical adsorption, intermolecular force, electrostatic force, etc. The fiber material includes hydrophilic polymers such as cellulose, nylon, polyvinyl alcohol or polyethylene glycol. The size of one magnetic particle is, for example, 0.1 to 10 μm. More preferably, 0.5 to 5 μm.

When a target is captured by covalent bonds, hydrolyzing a peptide bond included in the coating material, such as nylon, coating a surface of the magnetic particle results in generation of a functional group used for immobilization of biological material. In this case, functional groups that can be bound to biological material include a carboxyl group-COOH, an amino group-$NH_2$, and a thiol group and their derivative groups including homologous functional groups and different functional groups. Note that it is preferable to use an EDC as a crosslinking agent for a covalent bond.

When a target is captured by hydrogen bonding, there is a need to cause a bond via a hydrogen atom between atom X having more electronegative than a hydrogen, and, a material containing Y (nitrogen, oxygen, phosphorus, sulfur, halogen, etc.) coated on the surface of the magnetic particles. Moreover, for electrostatic coupling, it is necessary to coat the magnetic particles with ion crystalline material.

Also, there are cases where nucleic acid or fragment thereof having a base sequence having complementarity to a predetermined target nucleic acid or fragment thereof or a portion thereof is combined with the magnetic particles. At least two types of these magnetic particles may be used in combination.

The "amplification solution" includes, for example, in the case of performing amplification by the PCR method, DNA solution of a template to be amplified, primer solution, DNA polymerase solution, nucleotide solution, reaction buffer solution and the like. Also, solution for labeling may be included The "extraction reagent solution" allows proteins that form cell walls or the like contained in a sample to be decomposed or dissolved to cause nucleic acid or fragment thereof to be drained out of a bacteria or cells, thereby facilitating binding to the magnetic particles. The "extraction reagent solution" is mixed solution of: aqueous solution containing, for example, protease which is a proteolytic enzyme, chaotropic ions such as solution of guanidinium ions, urea ions or iodide ions, etc., and/or a surfactant for facilitating denaturation of the protein; buffer solution for facilitating the magnetic particles to capture the nucleic acid or a fragment thereof; and a binding promoter for promoting the magnetic particles to capture the nucleic acid or a fragment thereof. Incidentally, it may also include washing solution.

To facilitate extraction of the nucleic acid, it is preferable to repeat suction and discharge of the mixed solution by using a dispensing tip for capture and further to exert a magnetic field within the dispensing tip by the magnetic unit to cause the magnetic particles to be adsorbed on the inner wall thereof.

Fragmentation of nucleic acid and production of fragments may require "fragmentation solution" as well as "binding promoter" and "dissociation solution" as described below. Note that "having the number of bases within a predetermined range according to a sequencer" refers to a base sequence having the number of bases within a specified range according to contents of the sequencer performing genetic analysis of DNA or a fragment thereof and, for example, may include a whole range of the fragment having been fragmentated. Specifying the range of the number of bases in a base sequence is, for example, preset or set by a user every time via the operation unit for performing data input or commanding to an element (CPU+program) for performing information processing including a CPU provided in the sequencer pretreatment device. This element will be described later. The "fragmentation solution" is a chemical substance which causes cleavage of nucleic acid and includes, for example, aqueous solution containing transition metal-induced oxidative DNA cleavage substance. Specifically, transition metals include copper ions, iron ions, and nickel ions and for example, copper sulfate is used. Reducing agents include, for example, ascorbic acid, DTT, and mercaptoethanol. For example, aqueous solution containing sodium ascorbate is used. A concentration of the former is 1 m mol/L (liter) to 10 m mol/L while a concentration of the latter is 0.1 mmol/L to 4 mmol/L. These aqueous solutions allow for fragmentation in the range of 50 to 1000 base pairs (bp) depending on the concentration of the transition metal and the reducing agent and incubation time of several seconds to several minutes (the temperature range may be within 4° C. to 95° C.). That is, fragmentation is promoted when the concentration of the transition metal or the reducing agent is higher and the incubation time is longer. Cleavage of nucleic acid or a fragment thereof is carried out by generating a radical by reaction with the reducing agent and the transition metal.

The cleavage using the fragmentation solution has high uniformity compared to cleavage using a restriction enzyme since specificity of base sequence of the nucleic acid is not utilized and causes less damage compared to cleavage by ultrasound since no extra energy is applied.

The "binding promoter" is reagent that facilitates binding to the magnetic particles. For example, when the nucleic acid or a fragment thereof is captured by the magnetic particles by physical adsorption thereto, the "binding promoter" may be, for example, alcohols such as isopropyl alcohol or polymeric alcohols such as polyethylene glycol (PEG) and polyvinyl alcohols. The "dissociation solution" or elute that promotes dissociation or elution of bound material from magnetic particles is water when the nucleic acid or a fragment thereof, having been captured by the magnetic particles by physical adsorption, is to be dissociated therefrom. Note that, when the magnetic particles capture the nucleic acid or a fragment thereof by ionic bonding, the binding promoter and dissociation solution are a predetermined salt solution or aqueous solution having a predetermined pH.

To produce fragments of fragmentated nucleic acids, the fragment thereof is once bound to the magnetic particles coated with the silica, glass, cellulose or the like with the binding promoter by using the dispensing device, thereby capturing the fragment. Then, adding water which is the dissociation solution according to a predetermined range of molecular weight of a sequencer and thereby decreasing the concentration of the binding promoter, thereby causing the fragments to be dissociated from the magnetic particles. A fragment with a small molecular weight has weak bonding force to the magnetic particles, and thus is dissociated first. On the other hand, a fragment with a large molecular weight has strong bonding force to the magnetic particles, and thus is dissociated when the concentration of the binding promoter is considerably decreased. By leveraging this, if the range of molecular weight and the concentration of binding promoter are correlated in advance, a fragment having a molecular weight (number of bases in a base sequence) within a desired range (a predetermined range corresponding to a sequencer) may be produced. The dissociated fragment having the desired molecular weight is captured by adding other magnetic particles after removing the magnetic particles. Thereafter, the other magnetic particles are adsorbed on the inner wall by the magnetic unit, thereby recovering the fragments. Note that an exemplary relationship between the molecular weight and concentration is illustrated in FIG. 7. "Production" includes "selection", but also includes a case where production is performed without "selection" but by separation, capture, and the like.

The "amplification pretreatment step" is a step for dispensing solution containing the fragment having been fragmented and produced into the reaction vessel along with a predetermined amplification solution, whereby adapters (and primers) are bound to both ends of the fragment having been produced. Note that an amount to be amplified is 10 to 200 µL which can be manipulated in the reaction vessel for PCR, and thus dispensing tips for amplification, having a small capacity (e.g. a capacity of 100 µL) and capable of dispensing such an amount, is used. For this, dispensing tips used in the extraction and the like (e.g. a capacity of 1 mL) are removed and the dispensing tips for amplification having a small capacity is mounted to the nozzles.

To "detachably mount", for example, it is preferable to provide a detaching mechanism for detaching the dispensing tip from the nozzle to the nozzle head or a stage where the container group is provided. The "detaching mechanism" includes, for example, a mechanism where a plate, having a hole or a notched part therein having a diameter larger than an outer diameter of the nozzle but smaller than the thickest portion of the dispensing tip, is provided to the nozzle head or stage and the plate relatively ascends or descends along the axial direction of the nozzle extending through each of the holes, thereby detaching the mounted dispensing tip. Detachment is performed, for example, by linking the driving mechanism of a piston sliding within a cylinder, which is the suction and discharge mechanism, and the plate when the plate is provided in the nozzle head. When the plate is provided in the stage, detachment is performed by moving the nozzle upward and downward relative to the plate by a vertical moving mechanism.

Because of "causing relative movement among the nozzle and the container group', there are cases where the container group is fixed and the nozzle is moved, the nozzle is fixed and the container group is moved, and a combination thereof.

The nozzle or dispensing tip mounted to the nozzle reaches these containers by the moving mechanism, thereby allowing for sucking and discharging of liquid or mounting or detaching of the tip. Note that the nozzle is in communication with the suction and discharge mechanism, whereby sucking and discharging gas is performed. The suction and discharge mechanism will be described below. The "suction and discharge mechanism" includes a mechanism including, for example, a cylinder, a piston sliding within the cylinder, a nut part connected to the piston, a ball screw for screwing the nut part, and a motor for rotatably driving the ball screw in the forward and reverse directions and a pump mechanism.

Materials of containers or lids including the reaction vessel include, for example, resins such as polyethylene, polypropylene, polystyrene, and acrylic, glass, metal, metal compounds, and the like. The container is sized to be able to accommodate, for example, liquid of several to several hundreds microliters and to receive a tip of the dispensing tip therein. For example, when the container is cylindrical, for example, one container has a diameter of several to several tens millimeters and a depth of several to several tens millimeters.

The "dispensing tip" includes, for example, a thick tube, a thin tube, and a transition portion communicating the thick tube and the thin tube. The thick tube includes a mounting opening for receiving a lower end of the nozzle to allow the thick tube to be mounted to the nozzle. The thin tube includes a tip opening to allow liquid to flow in and out by suction and discharge of gas by the suction and discharge mechanism. The dispensing tip and nozzle may by manufactured from, for example, organic matter of resins such as polypropylene, polystyrene, polyester, acryl, or inorganic matter such as glass, ceramic, metal such as stainless steel, a metal compound, or semiconductor.

Note that the sequencer pretreatment device may include a "temperature controller" as necessary. The temperature controller includes a temperature source capable of increasing or decreasing the temperature within the reaction vessel containing liquid to be temperature-controlled based on an external signal or the like. The temperature source includes a block member provided with, for example, a Peltier element, a heater, and a cooling device or the like. To perform processing such as PCR, the temperature controller is preferably a thermal cycler using a Peltier element.

The "moving mechanism" includes, for example, a mechanism that causes relative movement among the reaction vessel, namely, the stage on which the reaction vessel is provided and the nozzle in the axial direction of the nozzle and on the horizontal plane. As movement on the horizontal plane, for example, there are an XY axes moving mechanism for allowing the stage or the nozzle to move along the Y-axis and X-axis and a Y (X) axis moving mechanism for allowing for movement along the Y-axis or X-axis. As movement in the axial direction of the nozzle, for example, there is a vertical moving mechanism provided to the nozzle head for allowing the nozzle to move in the axial direction thereof (Z axis direction).

Note that the fragmentation producing step in the sequencer pretreatment method preferably includes a selection step where a corresponding range of concentration of the binding promoter is defined based on a predetermined range corresponding to the sequencer and at least the fragmented nucleic acid, the magnetic particles, the binding promoter accommodated in the container group, and the dissociation solution are mixed, thereby producing solution having the range of concentration.

This allows the fragments having the molecular weight corresponding to the concentration to be dissociated from the magnetic particles in the solution (fragments of the other molecular weight remains bound to the magnetic particles) in the selection step. In the selection step, in order to recover the dissociated fragments, repeating suction and discharge of the solution while the magnetic unit exerts a magnetic field to the inside of the dispensing tip using the dispensing tip attached to the nozzle and the magnetic unit exerting a magnetic field to the inside of the dispensing tip is performed, thereby causing the magnetic particles to be adsorbed on the inner wall of the dispensing tip, removing the magnetic particles, and obtaining the fragments of abase sequence, in the residual liquid, having the number of bases within the predetermined range.

Here, a relationship between the range of number of bases in the base sequence and the range of concentration of the binding promoter is measured in advance in an experiment according to the concentration of the binding promoter. For example, FIG. 7 illustrates an example of the above. Based on the relationship, at least the amount and concentration of solution of the nucleic acid having been fragmentated, the magnetic particle suspension and the binding promoter solution, and those of the dissociation solution, which are to be mixed, are obtained by calculation or the like such that those of the dissociation solution corresponds to the range of concentration and each mixing ratio is obtained. Based on the mixing ratio, the suction and discharge mechanism, the nozzle head having the nozzle, the dispensing tip, the moving mechanism, the temperature controller and/or the magnetic unit of the sequencer pretreatment device are controlled to mix the above and to obtain the dissociated fragments of the predetermined range.

In this case, therefore, specifying the predetermined range of number of bases in the base sequence of the fragment according to the sequencer allows the range of concentration of the binding promoter to be defined. The mixed solution of a desired concentration is achieved by quantitative dispensing and the magnetic particles are removed and the fragments are dissociated therefrom in the residual liquid by allowing the magnetic particles to be adsorbed on the inner wall of the dispensing tip by the magnetic unit. This allows production of fragments, having a specified range of number of bases according to various sequencers, to be securely and easily implemented by simple control with high versatility.

A second aspect of the invention is the sequencer pretreatment method, using the sequencer pretreatment device further including a temperature controller capable of controlling the temperature in the reaction vessel, the method further including an amplification step of amplifying the produced fragment by controlling the temperature in the reaction vessel of the sequencer pretreatment device.

When the amplification step is not included as processing by a sequencer, pretreatment for a sequencer includes the amplifying step of amplifying the produced fragments.

The "temperature control" is to execute maintaining target liquid or a container at one or more predetermined temperatures having been set for a time having been set according to a defined order for a defined number of times. Commands to the temperature controller are performed by sending appropriate signals based on a program.

The "predetermined temperature" is a target temperature for a target object such as liquid to reach. For example, when nucleic acid of DNA or oligonucleotide or the like which is a fragment of the nucleic acid, included in the liquid is amplified by the PCR method, predetermined temperatures to be set are, for example, required temperatures for each of denaturation of DNA, annealing or hybridization, and elongation, namely, a temperature cycle of the PCR method, are approximately 94° C., a temperature between 50° C. to 60° C., for example, approximately 50° C., and approximately 72° C., respectively. On the other hand, when the SPIA method is performed, a constant temperature, for example, 55° C. or the like is set.

A third aspect of the invention is the sequencer pretreatment method, using the sequencer pretreatment device further including an optical measuring instrument for measuring an optical state in the various tips or the reaction vessel, the method further including a quality evaluation step of performing quality evaluation of a product having been obtained in at least one of the respective steps.

The "various tips" includes the dispensing tip as well as capillary electrophoresis tip.

The "capillary electrophoresis tip" includes a translucent capillary enclosing gel therein, a thick tube communicated to the capillary, an opening, provided at the lower end of the capillary, from which fluid can enter, and an opening provided at the upper end of the thick tube. The opening of the thick tube can be releasably supported by an electrode supporting member of the nozzle head by being mounted thereto. The electrode supporting member will be described later. Also, electrophoresis solution (buffer solution) can be introduced from the opening. When the tip is supported by the electrode supporting member after the electrophoresis solution is inserted into the thick tube, a first electrode provided to the electrode supporting member is inserted into the thick tube and may be in contact with the electrophoresis solution accommodated in the thick tube. Meanwhile, when the opening of the capillary is inserted into an electrode-attached liquid accommodating portion, provided with a second electrode, provided so as to be in contact with accommodated solution subjected to measurement, the solution subjected to measurement enters the opening. Applying a predetermined voltage between the first electrode and the second electrode allows an electric field to be exerted in the capillary electrophoresis tip, thereby allowing the charged nucleic acid or fragments to receive the force from the electric field to move within the gel. Incidentally, the capillary is a thin tube having an internal diameter of, for example, 0.05 to 0.5 mm, preferably 0.1 to 0.3 mm. Supporting or mounting of the capillary electrophoresis tip is performed by, for example, allowing the nozzle head to descend relative to the capillary electrophoresis tip accommodated in the container group and fitting and mounting the electrode supporting member or a cap to the opening. Mounting of the dispensing tip is also performed in a similar manner by allowing the nozzle head to descend and fitting the nozzle to the mounting opening of the dispensing tip. Detaching may be performed by using a tip detaching unit having a similar shape as that of the dispensing tip. Note that a power supply unit for applying a voltage between the first electrode and the second electrode is required.

The "quality evaluation step" is a step for performing an evaluation on the quality of a product generated as a result of the respective basic steps including the extraction step, fragmentation producing step, and amplification pretreatment step or the amplification step. This allows for ensuring that a result finally obtained has a high reliability, or, by checking which step includes an error in processing, thereby confirming the cause more easily and improving the quality of a product obtained as a result of the processing or step.

Evaluation of the quality is performed by measuring an optical state of the various tips or reaction vessel by the optical measuring instrument provided to the sequencer pretreatment device for evaluating the molecular weight or concentration of the nucleic acid or fragments having been obtained. For example, optically measuring nucleic acid or fragments thereof labeled by the electrophoresis method performed in the capillary electrophoresis tip allows a range of molecular weight to be analyzed, or optically measuring the absorbance allows the concentration of the nucleic acid or fragments thereof to be measured.

The "optical states" include luminescence, coloration, discoloration, and a variation of light where the "light variation" includes reflection, absorption, and scattering of light.

A fourth aspect of the invention is the sequencer pretreatment method, using the sequencer pretreatment device, further including, in at least one of the respective steps, a step of purifying nucleic acid or a fragment thereof in such a manner as to meet a processing object of each of the steps by mixing the product having been obtained as a result of the step with a predetermined magnetic particle suspension and repeating suction and discharge of the mixed solution via the dispensing tip mounted to the nozzle, thereby causing the magnetic particle to capture the nucleic acid or a fragment thereof and to be adsorbed on the inner wall of the dispensing tip using the magnetic unit.

Purification is performed with the sequencer pretreatment device for achieving the basic steps. Purification is not just repetition of the respective steps of the pretreatment but performed, preferably, with a different type of solution, different magnetic particles, or a different instrument. When performing the purification, the solution is washing solution, preferably, aqueous solution containing alcohols such as ethanol.

The purification is performed by repeating suction and discharge of solution while the nucleic acid or fragments thereof are adsorbed on the inner wall of the dispensing tip or suspended in the solution through magnetic particles and thereby removing proteins or impurities other than the nucleic acid or fragments thereof. Furthermore, impurities such as a primer and adapter that were not bound to the nucleic acid or the like in the amplification pretreatment step or amplification step can be removed.

A fifth aspect of the invention is the sequencer pretreatment method where, in at least one of the respective steps, evaluation of molecular weight of a product having been obtained as a result of the step is performed using the sequencer pretreatment device as the quality evaluation step.

A sixth aspect of the invention is the sequencer pretreatment method where, in at least one of the respective steps, evaluation of concentration of the nucleic acid or a fragment thereof is performed using the sequencer pretreatment device as the quality evaluation step.

In the evaluation of concentration, the absorbance of a solution containing the nucleic acid or fragments thereof is measured and thereby whether the concentration of the nucleic acid or fragments thereof meets a processing object of the step. In this manner, it is possible to evaluate the presence of impurities in each of the steps by using the device for performing the respective steps. Therefore, by determining whether to continue processing at an early stage, redoing the processing, additional processing, or halting the processing may be decided on and thus reliable processing may be performed with high efficiency.

According to the present aspect of the invention, using the device incorporated to the sequencer pretreatment device for performing the basic steps of the extraction step, the fragmentation producing step, and the amplification pretreatment step or the amplification process, purification or determination of the molecular weight or concentration can be executed easily and efficiently, thereby allowing the evaluation of the quality to be reflected to the processing easily and efficiently.

A seventh aspect of the invention is the sequencer pretreatment method using the sequencer pretreatment device where: one or more capillary electrophoresis tips including a capillary and a thick tube, communicating with the capillary, sealed with gel, are accommodated in the container group; the nozzle head has one or more electrode supporting members, which can support the capillary electrophoresis tip on the side of the thick tube, are provided with a first electrode that may be in contact with electrophoresis solution accommodated in the thick tube, and are made movable relative to the container group together with the nozzle by the nozzle moving mechanism; and the container group further includes one or more electrode-attached liquid accommodating portions having a second electrode provided thereto in such a manner as to be in contact with liquid accommodated therein, where, in the quality evaluation step, evaluation of molecular weight is performed by dispensing the electrophoresis solution from the liquid accommodating portion provided to the container group for accommodating the electrophoresis solution into the thick tube, supporting the capillary electrophoresis tip by the electrode supporting member on the side of the thick tube and thereby allowing the solution to be in contact with the electrode, extracting, dispensing into the electrode-attached liquid accommodating portion, and labeling a product having been obtained as a result of each of the steps, inserting a tip of the capillary into the electrode-attached liquid accommodating portion, and thereby exerting an electric field to the inside of the tip via the electrodes, and measuring the inside of the capillary by the optical measuring instrument.

Here, "electrophoresis solution" includes agarose gel and 1×TAE buffer solution or 1×TBE buffer solution used for electrophoresis. Moreover, it may also include labeling reagent solution. "Labeling" is performed by, for example, labeling fragmentated nucleic acid or fragments thereof with fluorescence by an intercalator. The intercalator utilizes a character that a fluorescent substance such as the SYBR (registered trademark) GREEN I and ethidium bromide enters the double-stranded DNA and emits fluorescence.

Voltage applied between the electrodes is, for example, approximately several to several thousand volts.

Since the capillary electrophoresis tip, sealed with the agarose gel and accommodated in the container group such that the tip can be mounted to the electrode supporting member, is supported by the electrode supporting member provided to the nozzle head by being mounted thereto, etc. by descending movement of the nozzle head using the sequencer pretreatment device for performing the respective basic steps, thereby allowing the acceptability of the molecular weight to be determined, the result can be immediately applied to the next step and thus the processing can be performed efficiently and rapidly with a high-accuracy.

An eighth aspect of the invention is the sequencer pretreatment method where the amplification step includes an internal control measuring step of measuring an internal control nucleic acid or fragment thereof included in the nucleic acid or fragment thereof using the sequencer pretreatment device as the quality evaluation step.

Here, "internal control nucleic acid or fragments thereof" is nucleic acid or fragments thereof added in order to determine whether the PCR reaction itself is inhibited. When the internal control nucleic acid or fragments thereof are added, the PCR reaction is determined as being normal if amplification of the internal control nucleic acid or fragments thereof is acknowledged. The PCR reaction is determined as being inhibited if amplification is not acknowledged in both of a target and the internal control nucleic acid or fragments thereof.

A ninth aspect of the invention is the sequencer pretreatment device including: a suction and discharge mechanism for sucking and discharging gas; a nozzle head having one or more nozzles for detachably mounting a dispensing tip communicated with the suction and discharge mechanism and capable of sucking and discharging liquid; a container group including at least a reaction vessel and liquid accommodating portions containing various liquids including magnetic particle suspension; a moving mechanism for causing relative movement among the nozzle and the container group; and a magnetic unit capable of exerting and removing a magnetic field from outside to and from the dispensing tips mounted to the nozzles, and further including a control unit for controlling at least the suction and discharge mechanism, moving mechanism, and magnetic unit based on an external signal. The control unit includes: an extraction control unit for mixing and stirring a sample, extraction reagent solution, and magnetic particle suspension accommodated in the container group and extracting nucleic acid; a fragmentation producing control unit for fragmentating the extracted nucleic acid by mixing with fragmentation solution accommodated in the container group and producing, from the fragmentated nucleic acid, a fragment of base sequence having the number of bases within a predetermined range corresponding to a sequencer using magnetic particle suspension; and an amplification pretreatment control unit for controlling such that a predetermined volume of solution containing the produced fragment is dispensed by the predetermined dispensing tip into the reaction vessel together with amplification solution for mixing therewith.

Here, a temperature controller capable of controlling the temperature in the reaction vessel is provided as necessary.

The control unit includes a computer (CPU) incorporated in the sequencer pretreatment device and a program for driving the computer. For example, the suction and discharge mechanism, the moving mechanism, and the magnetic unit or, if necessary, the temperature controller are controlled with signals via a DA converter and an AD converter.

Specifically, the extraction control unit controls to perform extraction by sucking and discharging the sample, extraction reagent solution, and magnetic particle suspension from and into the reaction vessel using the dispensing tip mounted to the nozzle, suction and discharge mechanism, and moving mechanism for mixing and stirring therein, and if necessary binding the nucleic acid having been obtained from the sample to the magnetic particles using the temperature controller, and exerting a magnetic field to the dispensing tip by the magnetic unit, thereby allowing the magnetic particles to be adsorbed on the inner wall thereof.

Specifically, the fragmentation producing control unit performs fragmentation by sucking and discharging the extracted nucleic acid and fragmentation solution via the dispensing tip by the suction and discharge mechanism for mixing in the reaction vessel, and if necessary, causing reaction in the reaction vessel for a predetermined incubation time using the temperature controller. Increasing the incubation time or concentration of the fragmentation solution increases cleavage portions and thus results in a smaller molecular weight of the fragments. Next, mixing the magnetic particle suspension and the fragments and further mixing binding promoter allows substantially all of the fragments to be bound to the magnetic particles. Thereafter, dispensing a predetermined amount of the dissociation solution and varying the concentration of the binding promoter allows the fragments having the number of bases within a range corresponding to the concentration to be dissociated. Lower the concentration of the binding promoter is, the larger number of bases are included in a fragment. As described above, the fragmentation producing control unit includes data such as a table, for example, corresponding to FIG. 7, showing a relationship between a range of concentration of the binding promoter and a range of molecular weight of the fragments of the nucleic acid (which corresponds to the number of bases in a base sequence).

The amplification pretreatment control unit dispenses a predetermined amount of solution containing the produced fragments, namely, an amount that can be operated in a PCR reaction vessel, for example, the total amount of 10 to 200 µL into the reaction vessel. For this, a dispensing tip having a small capacity (e.g. 5 to 500 μL, preferably 10 to 100 μL) is mounted to the nozzle for use.

Specifically, the container group preferably includes at least the liquid accommodating portion for accommodating a sample, the liquid accommodating portion for accommodating extraction reagent solution for extracting nucleic acid from the sample, the liquid accommodating portion for accommodating the fragmentation solution required for fragmentating the extracted nucleic acid into fragments having the number of bases within a predetermined range, the liquid accommodating portion for accommodating magnetic particle suspension suspending magnetic particles capable of binding with respective nucleic acid or fragments thereof, each of the liquid accommodating portions for accommodating the binding promoter solution for promoting binding between the nucleic acid or fragments thereof and the magnetic particles or the dissociation solution, the liquid accommodating portion for accommodating the amplification solution, the reaction vessel temperature of which is controllable, and the tip accommodating portion for detachably accommodating or holding the dispensing tip in the nozzle. Furthermore, the liquid accommodating portion for accommodating the electrophoresis solution is required when acceptability of a molecular weight is determined. The electrophoresis solution will be described later.

When using two or more nozzles, by respectively arranging the container group, having two or more accommodating portions each corresponding to each of the nozzles, in two or more exclusive portions each corresponding to each of the nozzles such that one of the nozzles enters while another nozzle is prevented from entering, each of the exclusive portions is set to every different sample. This ensures preventing cross contamination.

A tenth aspect of the invention is the sequencer pretreatment device further including a temperature controller capable of controlling the temperature in the reaction vessel, where the control unit further includes an amplification control unit for amplifying the produced fragment by controlling the temperature in the reaction vessel.

When the amplification control unit is not included in a configuration of a sequencer, pretreatment for the sequencer includes the amplifying step of amplifying the produced fragments.

Note that, in the sequencer pretreatment device, it is preferable that the container group accommodates each of the binding promoter solution and the dissociation solution as the various liquids and that the fragmentation producing control unit includes a selection control unit for controlling the suction and discharge mechanism, moving mechanism, temperature controller, and/or magnetic unit such that the fragmentated nucleic acid, magnetic particles, binding promoter, and dissociation solution are mixed to produce solution based on a range of concentration of the binding promoter corresponding to a predetermined range of the number of bases in a base sequence corresponding to the sequencer.

Here, a relationship between the range of number of bases in the base sequence and the range of concentration of the binding promoter is measured in advance in an experiment according to the concentration of the binding promoter. For example, FIG. 7 illustrates an example of the above. By storing data including such a table in a memory included in an element (CPU+program) for performing information processing of the sequencer pretreatment device, as the fragmentation producing control unit, the range of concentration of the binding promoter is defined. As a result, at least the amount and concentration of solution of the nucleic acid having been fragmentated, the magnetic particle suspension and the binding promoter solution, and those of the dissociation solution, which are to be mixed, are obtained by calculation or the like such that those of the dissociation solution corresponds to the range of concentration and each mixing ratio is obtained. Based on the mixing ratio, the suction and discharge mechanism, the nozzle head having the nozzle, the moving mechanism, the temperature controller and/or the magnetic unit of the sequencer pretreatment device are controlled to mix the above and to obtain the fragments of the predetermined range dissociated into the solution. Therefore, production of fragments having the number of bases within a specified range corresponding to various sequencers can be reliably and easily achieved by the simple control with a high versatility.

An eleventh aspect of the invention is the sequencer pretreatment device further including an optical measuring instrument for measuring an optical state in the various tips or the reaction vessel, where the control unit further includes a quality evaluation control unit for controlling the optical measuring instrument based on an external signal and performing, for at least one of the respective control units, quality evaluation of a product having been obtained as a result of control by the control unit.

The "various tips" refers to a variety of dispensing tips (including a dispensing tip of a normal volume of 0.5 to 50 mL or dispensing tip of the aforementioned small volume, etc.) or a capillary electrophoresis tip as previously described.

A twelfth aspect of the invention is the sequencer pretreatment device, where the control unit further includes a purification control unit for controlling such that the nucleic acid or a fragment thereof is purified by mixing and stirring solution, containing the nucleic acid or a fragment thereof, with the magnetic particle suspension by sucking and discharging, allowing the magnetic particle to capture the target nucleic acid or a fragment thereof, exerting a magnetic field to the inside of the dispensing tip and thereby allowing the capturing magnetic particles to be adsorbed on the inner wall thereof.

The magnetic particles used by the purification control unit are preferably different from the magnetic particles used by the extraction control unit, fragmentation producing control unit, amplification pretreatment control unit, or amplification control unit. Here, for example, it may be controlled such that the magnetic particles are sucked and discharged together with solution of a predetermined ratio of the dissociation solution and binding promoter, extraction reagent solution, fragmentation solution, or the washing solution, etc. Here, the washing solution is preferably aqueous solution containing alcohols such as ethanol.

A thirteenth aspect of the invention is the sequencer pretreatment device, where: one or more capillary electrophoresis tips including a capillary and a thick tube, communicating with the capillary, sealed with gel, are accommodated in the container group; the nozzle head has one or more electrode supporting members, which can support the capillary electrophoresis tip on the side of the thick tube, are provided with a first electrode that may be in contact with electrophoresis solution accommodated in the thick tube, and are made movable relative to the container group together with the nozzle by the moving mechanism; and the container group further includes one or more electrode-attached liquid accommodating portions having a second electrode provided thereto that may be in contact with liquid accommodated therein. A power for electrophoresis connected between the first electrode and the second electrode whereby voltage for electrophoresis is applied.

A fourteenth aspect of the invention is the sequencer pretreatment device, where the optical measuring instrument is provided such that the absorbance of the inside of one or more translucent liquid accommodating portions provided to the container group can be measured; and the quality evaluation control unit allows solution containing a product having been generated by each of the control units to be accommodated in each of the liquid accommodating portions and causes the optical measuring instrument to measure the absorbance of each of the liquid accommodating portions.

A fifteenth aspect of the invention is the sequencer pretreatment device, where the quality evaluation control unit controls such that evaluation of molecular weight is performed by dispensing the electrophoresis solution from the liquid accommodating portion for accommodating the electrophoresis solution provided to the container group into the thick tube, supporting the capillary electrophoresis tip by the electrode supporting member on the side of the thick tube and thereby allowing the solution to be in contact with the electrode, extracting, dispensing into the electrode-attached liquid accommodating portion, and labeling a product having been obtained as a result of each of the steps, inserting a tip of the capillary into the electrode-attached liquid accommodating portion, and thereby exerting an electric field to the tip via the electrodes, and measuring the inside of the capillary by the optical measuring instrument.

A sixteenth aspect of the invention is the sequencer pretreatment device where the first electrode is mounted to an electrode mounting portion of the electrode supporting member in an electrically conductive manner.

A seventeenth aspect of the invention is the sequencer pretreatment device, where: the electrode supporting member includes a cap covering a tip of the electrode supporting member; the first electrode of the electrode supporting member projects from the cap by penetrating therethrough; and the capillary electrophoresis tip is attached to the cap, thereby sealing an opening of the tip.

An eighteenth aspect of the invention is the sequencer pretreatment device including: one or more flexible light guiding paths, each having a front end and a rear end, the front end provided in proximity to or in contact with the capillary of one or more capillary electrophoresis tips and along the capillary in a movable manner, or in proximity to or in contact with a side surface of one or more translucent reaction vessels; an array body where the rear ends are arranged along a predetermined path; and the optical measuring instrument sequentially connectable to the rear end in an optical manner and relatively movable along the predetermined path of the array body.

"Relatively movable" includes cases where the optical measuring instrument moves relative to the array body and the array body moves relative to the optical measuring instrument. Furthermore, there are cases where the optical measuring instrument and array body are provided on the stage and the optical measuring instrument and array body are provided to the nozzle head.

A nineteenth aspect of the invention is an electrophoresis device including: one or more capillary electrophoresis tips including a translucent capillary and a thick tube, communicating with the capillary, sealed with gel; one or more electrode supporting members movable relative to the capillary electrophoresis tip, the electrode supporting member provided with a first electrode that may be in contact with electrophoresis solution and capable of supporting the capillary electrophoresis tip on the side of the thick tube; and one or more electrode-attached liquid accommodating portions having a second electrode provided thereto such that the second electrode may be in contact with liquid accommodated therein.

Incidentally, it is preferable that the optical measuring instrument for measuring an optical state in the capillary is provided. Moreover, the electrode supporting member is preferably provided to the nozzle head in conjunction with the nozzle. According to the present aspect of the invention, the capillary electrophoresis tip can be used in a disposable manner with respect to the electrode supporting member, thereby allowing for easy operation, preventing cross contamination, and having high reliability.

Advantageous Effects of Invention

According to the first, second, ninth, or tenth aspect of the invention, the pretreatment for a sequencer, including extraction of nucleic acid or fragments thereof from a sample, fragmentation of nucleic acid and production of fragments having the number of bases within a predetermined range corresponding to a sequencer, and amplification pretreatment or amplification processing, can be executed efficiently and easily without increasing the scale of the device by using the magnetic particles of the same type having binding property with the nucleic acid or fragments thereof, nozzle head, suction and discharge mechanism, container group for accommodating a sample and reagent required, moving mechanism, and magnetic unit, or the temperature controller.

According to the third or eleventh aspect of the invention, evaluation of the quality of pretreatment can be also controlled only by further including the optical measuring instrument in addition to the aforementioned combination including the magnetic particles. Therefore, without increasing the scale of the device unreasonably, the pretreatment for a sequencer can be performed with a high reliability with a simple structure.

According to the fourth or twelfth aspect of the invention, by performing the pretreatment for a sequencer using the combination while executing the purification step of removing impurities by repeating suction and discharge, while the target nucleic acid or fragments thereof are bound to the magnetic particles, in at least one of the respective steps, the reliability of the entire pretreatment can be enhanced easily in a simple manner.

According to the fifth, seventh, thirteenth, fifteenth, or eighteenth aspect of the invention, by performing evaluation of the molecular weight on the nucleic acid or fragments thereof having been produced as a result of the respective steps of the pretreatment for a sequencer or by processing by the control unit using the combination including the magnetic particles, the quality thereof can be evaluated easily in a simple manner, thereby enhancing the reliability.

According to the sixth or fourteenth aspect of the invention, by performing evaluation of the concentration of the nucleic acid or fragments thereof using the combination regarding sequencer pretreatment, a presence of impurities is determined in at least one of the respective steps, thereby improving the quality and enhancing the reliability.

According to the eighth aspect of the invention, in the pretreatment for the sequencer, measuring the internal control allows for determining of whether the PCR reaction itself is inhibited, thus enhancing reliability.

According to the sixteenth aspect of the invention, by attaching the electrode, which may be in contact with the sample or the extracted nucleic acid or fragments thereof, to the electrode supporting member in a removable manner, cross contamination or environmental pollution can be prevented without replacing the nozzle head itself but only by replacing the electrode.

According to the seventeenth aspect of the invention, sealing the capillary electrophoresis tip by the cap and thereby preventing the electrode supporting member from being in contact with the nucleic acid or fragments thereof allows for facilitating of reuse and preventing of cross contamination or environmental pollution.

According to the eighteenth aspect of the invention, the capillary electrophoresis tips arranged at predetermined intervals or the reaction vessel and the array body are optically connected via a flexible light guiding path. Therefore, the predetermined path moving relative to the optical measuring instrument can be arranged while the rear ends of the light guiding paths are integrated in intervals shorter than the predetermined intervals, thereby shortening a relative moving distance of the optical measuring instrument. Furthermore, executing measurement of the molecular weight and measurement of the amplification reaction in the reaction vessel by the same optical measuring instrument allows quality evaluation to be efficiently performed without increasing the scale of the device.

DESCRIPTION OF EMBODIMENTS

Next, embodiments of the present invention will be described with reference to the drawings. Note that these embodiments are not to be construed as limiting the present invention unless otherwise specified. Also, identical elements in the respective embodiments are denoted with the same signs and a description thereof is omitted.

Figure 1:
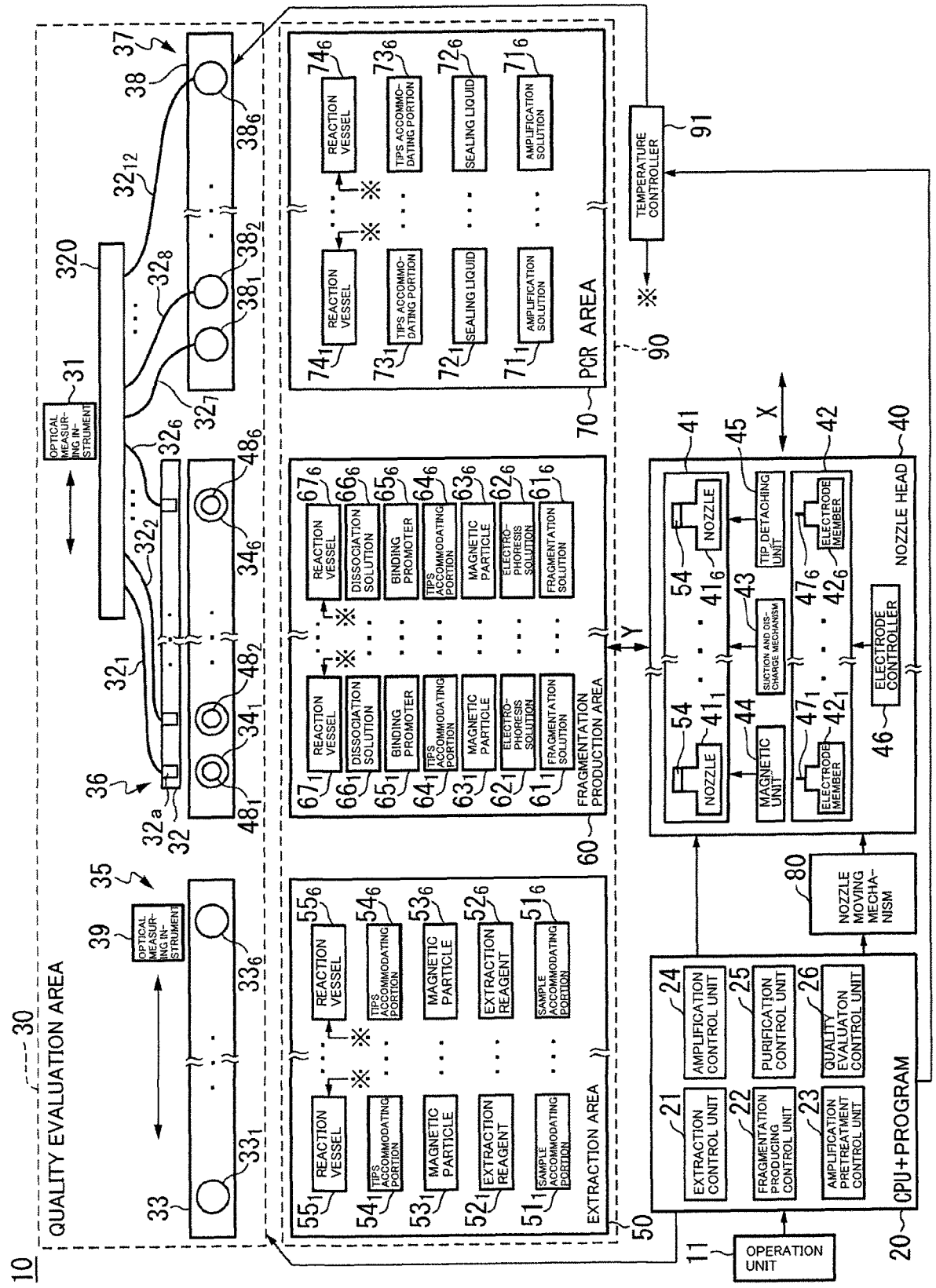
FIG. 1 is a block diagram illustrating a sequencer pretreatment device according to an embodiment of the present invention.

FIG. 1 is a block diagram illustrating a sequencer pretreatment device 10 according to an embodiment of the present invention.

The sequencer pretreatment device 10 according to the present embodiment includes a nozzle head 40 having a plurality of nozzles $41_1$ to $41_6$ (six nozzles in this example) for detachably mounting, at a mounting opening thereof, a plurality of dispensing tips 49 (six tips in this example) capable of sucking and discharging liquid by a suction and discharge mechanism 43 for sucking and discharging gas, an accommodating portion group 90 including a reaction vessel and a liquid accommodating portion for accommodating various liquids including magnetic particle suspensions 53 and 63, a nozzle moving mechanism 80 relatively movable between the nozzles $41_1$ to $41_6$ provided to the nozzle head 40 and the accommodating portion group 90, a temperature controller 91 capable of controlling temperature in the reaction vessel, a quality evaluation area 30 for evaluating quality of a resulting product from the treatment, a magnetic unit 44, provided to the nozzle head 40, capable of exerting and removing a magnetic field to and from the six dispensing tips 54 mounted to the nozzles $41_1$ to $41_6$ from outside, a CPU+program 20 for performing information processing for controlling, by an external signal, the suction and discharge mechanism, the nozzle moving mechanism, and the magnetic unit, and an operation unit 11 for giving an order to the CPU+program 20 and inputting data. The nozzle moving mechanism corresponds to the moving mechanism. Also, a combination of the accommodating portion group 90 and the quality evaluation area 30 corresponds to the container group.

The nozzle head 40 includes the plurality of nozzles $41_1$ to $41_6$ (six nozzles in this example), a nozzle array substrate 41 where the nozzles $41_1$ to $41_6$ are arranged in a row at predetermined intervals, the magnetic unit 44, the suction and discharge mechanism 43, a tip detaching unit 45 for detaching the dispensing nozzles $41_1$ to $41_6$ mounted to the tips of the nozzles $41_1$ to $41_6$, electrode supporting members $42_1$ to $42_6$, for mounting and supporting capillary electrophoresis tips $64_1$ to $64_6$ in mounting openings thereof, provided such that first electrodes $47_1$ to $47_6$ protrude from the tip, a supporting member array board 42 where the electrode supporting members $42_1$ to $42_6$ are arranged in a row at predetermined intervals, and an electrode controller 46 for controlling such that an electric field is generated by applying a predetermined voltage between the first electrodes $47_1$ to $47_6$ and second electrodes $48_1$ to $48_6$ provided in the electrode-attached liquid accommodating portions $34_1$ to $34_6$. The capillary electrophoresis tip 64 and electrode-attached liquid accommodating portions $34_1$ to $34_6$ will be described later.

The accommodating portion group 90 includes: an extraction area 50 where each of the reaction vessels and the accommodating portions for accommodating a sample, extraction reagent solution for extracting nucleic acid from the sample, magnetic particle suspension, and a dispensing tip, etc. is arranged at predetermined column intervals along the array direction (column direction) of the nozzles $41_1$ to $41_6$ of the nozzle head 40, forming a matrix shape as a whole; a fragmentation production area 60 where each of the reaction vessel and the accommodating portions accommodating fragmentation solution for fragmentating the extracted nucleic acid and producing fragments, the magnetic particle suspension, binding promoter, dissociation solution, electrophoresis solution, and capillary electrophoresis tip is arranged at the column intervals along the array direction of the nozzle head 40, forming a matrix shape as a whole; and a PCR area 70 where each of the reaction vessel and the accommodating portions accommodating amplification solution for performing amplification pretreatment of the fragmentated fragments and amplification processing, sealing liquid, and the dispensing tip is arranged at the intervals of the nozzle head 40 along the column direction, forming a matrix shape as a whole.

The quality evaluation area 30 includes: an absorbance measuring area 35 for measuring the absorbance of solution containing nucleic acid or fragments thereof; a molecular weight evaluation area 36 for performing evaluation of molecular weight of the nucleic acid or fragments thereof by electrophoresis using the capillary electrophoresis tip; and an internal control measuring area 37 for measuring the amount of amplification of an internal control fragment contained in the amplified fragments labeled with fluorescence.

The CPU+program 20 and the operation unit 11 correspond to a main body of an information processing device and a keyboard, touch screen, mouse, liquid crystal panel or the like, respectively. The CPU+program 20 performs control by sending and receiving a signal to the suction and discharge mechanism 43, the nozzle moving mechanism 80, the magnetic unit 44, and the temperature controller 91 via a DA converter and an AD converter upon a command from the operation unit 11.

Furthermore, based on FIG. 1, the aforementioned extraction area 50, fragmentation production area 60, PCR area 70, absorbance measuring area 35, molecular weight evaluation area 36, internal control measuring area 37, and CPU+program 20 will be described specifically.

The extraction area 50 includes: sample accommodating portions $51_1$ to $51_6$ for accommodating six types of samples 51 arranged at the predetermined column intervals in the column direction of the nozzles $41_1$ to $41_6$; extraction reagent accommodating portions $52_1$ to $52_6$ for accommodating the extraction reagent solution 52 including a proteolytic enzyme (proteases) that destroys the cell and releases nucleic acid, chaotropic ion solution, the binding promoter for the magnetic particles such as polyethylene glycol or the like; magnetic particle suspension accommodating portions $53_1$ to $53_6$, for accommodating the magnetic particle suspension 53 where magnetic particles coated with cellulose are suspended, arranged at the column intervals along the column direction; tips accommodating portions $54_1$ to $54_6$ for accommodating the dispensing tip 54, having a capacity of 1 mL, accommodated with a mounting opening facing up so as to be mountable to the nozzles $41_1$ to $41_6$ arranged at the column intervals along the column direction and a perforating tip for perforating a seal on a prepacked well; and translucent reaction vessels $55_1$ to $55_6$, temperature of which can be controlled by the temperature controller 91, arranged at the column intervals along the column direction. Also, it is preferable that the cleaning fluid containing alcohols such as ethanol is arranged while being accommodated in the liquid accommodating portion in a similar manner. The extraction reagent solution 52 may be obtained by accommodating each component such as an enzyme separately in the liquid accommodating portion and mixing just before use in the extraction reagent accommodating portion.

The fragmentation production area 60 includes: fragmentation solution accommodating portions $61_1$ to $61_6$ for accommodating the fragmentation solution 61 for fragmentating nucleic acid, for example, the fragmentation solution including copper sulphate and aqueous solution of sodium ascorbate; electrophoresis solution accommodating portions $62_1$ to $62_6$ for accommodating the electrophoresis solution 62; magnetic particle suspension accommodating portions $63_1$ to $63_6$ for accommodating the magnetic particle suspension 63 used for binding with fragments having the number of bases within a predetermined range corresponding to a sequencer (that is, a desired range of a user) from among the fragments of nucleic acid; tips accommodating portions $64_1$ to $64_6$ for accommodating the capillary electrophoresis tip 64 and dispensing tip or the like; binding promoter solution accommodating portions $65_1$ to $65_6$ for accommodating the binding promoter solution 65 for promoting binding to the magnetic particles such as polyethylene glycol; dissociation solution accommodating portions $66_1$ to $66_6$ for accommodating the dissociation solution 66 including, for example, water; and the reaction vessels $67_1$ to $67_6$.

The PCR area 70 includes: amplification solution accommodating portions $71_1$ to $71_6$ for accommodating the amplification solution 71 including primer solution, DNA polymerase, nucleotide solution or the like; sealing liquid accommodating portions $72_1$ to $72_6$ for accommodating sealing liquid 72 for sealing the reaction vessel; dispensing tips accommodating portions $73_1$ to $73_6$ for accommodating the dispensing tip 73 having a small capacity (e.g. 100 μL); and reaction vessels $74_1$ to $74_6$, having a capacity of approximately 10 μL, temperature of which is controlled by the temperature controller 91. The sealing liquid includes, for example, mineral oil and silicone oil. The "mineral oil" is derived from petroleum and the "silicone oil" is an oily substance composed of a molecule of linear structure having 2000 or less siloxane bonds. Note that, the capacity of the liquid accommodating portions of the extraction area 50, fragmentation production area 60, and PCR area 70 is preferably approximately 200 μL to 2 mL.

The absorbance measuring area 35 of the quality evaluation area 30 has translucent liquid accommodating portions $33_1$ to $33_6$ arranged, for example on the sequence substrate 33, at the predetermined intervals along the column direction and is provided with an optical measuring instrument 39, movable in such a manner as to pass through the proximity of a side surface of each of the liquid accommodating portions $33_1$ to $33_6$, for measuring the absorbance (OD value) of liquid accommodated in each of the liquid accommodating portions $33_1$ to $33_6$.

The molecular weight evaluation area 36 has translucent electrode-attached liquid accommodating portions $34_1$ to $34_6$ each provided with the second electrodes $48_1$ to $48_6$ in a contactable manner with liquid accommodated in the bottom part thereof. These electrode-attached liquid accommodating portions $34_1$ to $34_6$ are arranged, for example on the sequence substrate 34 in a line shape, at the predetermined intervals along the column direction.

In a use state where a tip of the capillary electrophoresis tip 64 is inserted in the electrode-attached liquid accommodating portions $34_1$ to $34_6$, the molecular weight evaluation area 36 includes: light guiding paths $32_1$ to $32_6$ of optical fibers, having measuring ends $32_1a$ to $32_6a$ on one end and connection ends on the other end, provided along the axial direction of the electrophoresis tip 64 to allow for vertical movement; a measuring end array body 32 arranging the measuring ends $32_1a$ to $32_6a$ along the column direction at the predetermined intervals and supporting the measuring ends in such a manner to allow for vertical movement; a connection end array body 320 arranging the connection ends at intervals shorter than the predetermined intervals; and an optical measuring instrument 31, provided to allow for movement along the connection end array body 320, for receiving and emitting light by being sequentially and optically connected to the arrayed connection ends.

In the internal control measuring area 37, translucent reaction vessels $38_1$ to $38_6$ for PCR amplification are surrounded by a temperature control block, temperature of which can be controlled by the temperature controller 91, and arranged on an array substrate 38 in a line shape along the column direction at the predetermined intervals in such a manner as to be in contact with the temperature control block.

Also, the internal control measuring area 37 has light guiding paths $32_7$ to $32_{12}$ of optical fibers, having measuring ends on one end and connection ends on the other end, provided in contact with or in the proximity of the reaction vessels $38_1$ to $38_6$. The connection ends arranged on the connection end array body 320 at intervals shorter than the predetermined intervals in a line shape in conjunction with the aforementioned plurality of (six in this example) connection ends. A total of twelve connection ends are sequentially and optically connected with the optical measuring instrument 31.

The CPU+program 20 includes: an extraction control unit 21 for mixing and stirring a sample 51, extraction reagent solution 52, and magnetic particle suspension 53 accommodated in the extraction area 50 to extract nucleic acid; a fragmentation producing control unit 22 for fragmentating the extracted nucleic acid by mixing with fragmentation solution 61 accommodated in the fragmentation production area 60 and producing a fragment of base sequence having the number of bases within a predetermined range corresponding to a sequencer using magnetic particle suspension 63; an amplification pretreatment control unit 23 for controlling such that a predetermined volume of solution containing the produced fragment is dispensed together with amplification solution 71, accommodated in the PCR area 70, into the reaction vessels $74_1$ to $74_6$ for mixing therein by replacing with a dispensing tip 73 of a small capacity (e.g. in the order of 10 μL) corresponding to the nozzles $41_1$ to $41_6$: an amplification control unit 24 for performing amplification by controlling the temperature in the reaction vessels $74_1$ to $74_6$ by the temperature controller 91: a purification control unit 25 for purifying nucleic acid or fragments thereof in such a manner as to meet each processing object by mixing the product obtained through control by each of the control units with the predetermined magnetic particle suspensions 53 and 63 and causing the magnetic particles to be adsorbed on the inner wall of the dispensing tip using a new dispensing tip 54 mounted to the nozzles $41_1$ to $41_6$; and a quality evaluation control unit 26 for performing, for at least one of the respective control units, quality evaluation of a product having been obtained as a result of control by the control unit using the optical measuring instrument for measuring an optical state in the capillary electrophoresis tip or the reaction vessel. The fragmentation producing control unit 22 includes the selection control unit.

Figure 2:
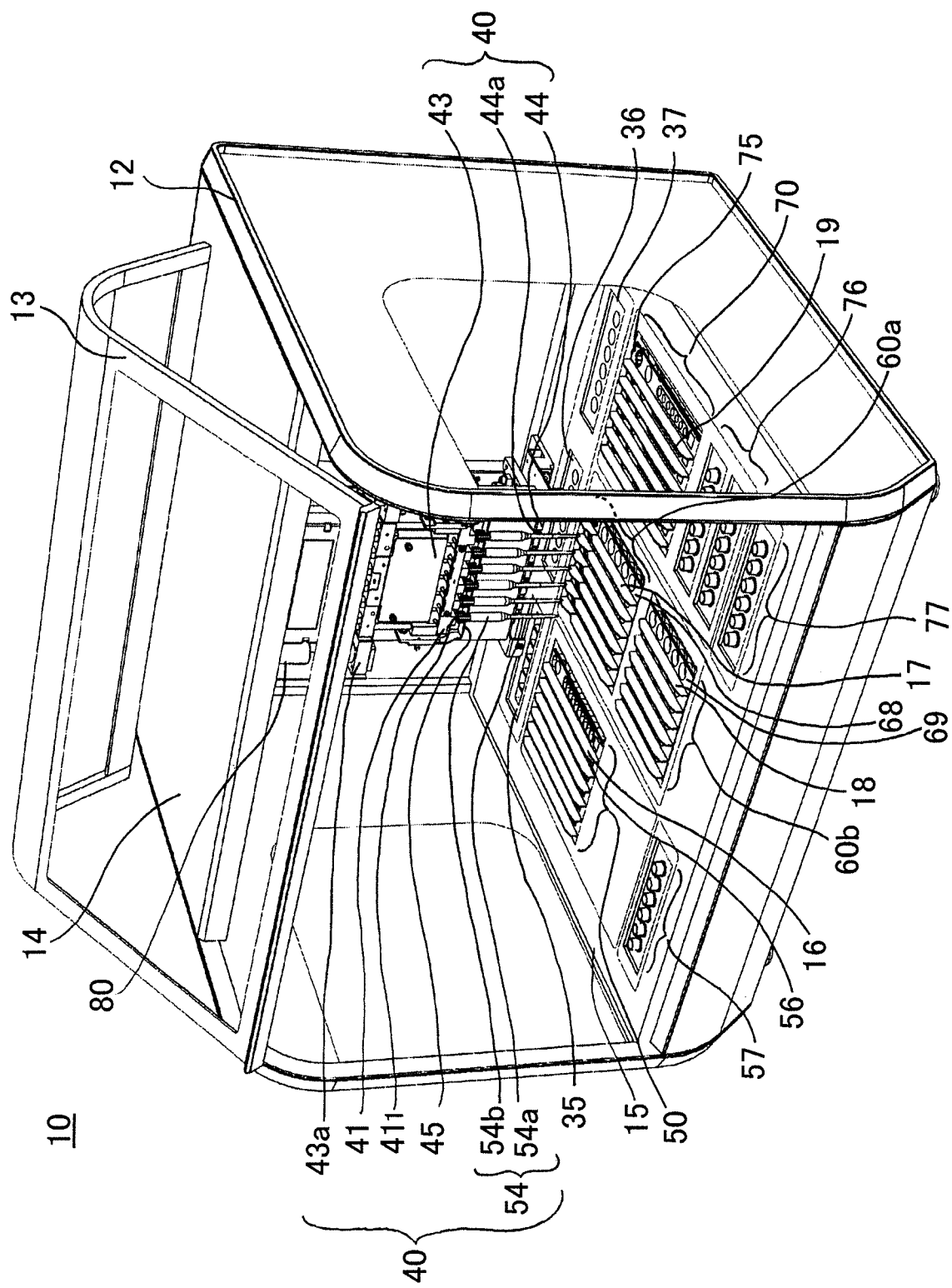
FIG. 2 is an overall perspective view illustrating a sequencer pretreatment device according to an embodiment of the present invention.

FIG. 2 is an overall perspective view of the sequencer pretreatment device 10 according to the embodiment of the present invention illustrated in FIG. 1.

The sequencer pretreatment device 10 according to the present embodiment is surrounded by a casing 12, covered with a top plate 14 in the upper face thereof, with a removable door 13 attached to the front face thereof. The door 13 has, for example, approximately a length of 600 mm (X axis direction), a depth of 600 mm (Y axis direction), and a height of 500 mm (Z axis direction). The casing 12 is, as described above, provided with: the nozzle head 40 provided in such a manner as to be suspended from the top plate 14 via the nozzle moving mechanism 80; and a stage 15 where the quality evaluation area 30 as the container group, the absorbance measuring area 35 belonging respectively to the accommodating portion group 90, the molecular weight evaluation area 36, the internal control measuring area 37, and the extraction area 50, the fragmentation production area 60, and the PCR area 70 belonging to the accommodating portion group 90 are provided. Noted that the operation unit 11 and the CPU+program 20 are also incorporated into a side wall and the inside of the casing 12.

The extraction area 50 is provided with six cartridge containers 56 arranged in parallel along the Y axis direction and partition walls 16, provided between adjacent cartridge containers 56, for preventing contamination by scattering of liquid upon suction or discharge or movement of the dispensing tip. Twelve wells or holes in each of the cartridge containers 56 correspond to the aforementioned sample accommodating portion, extraction reagent accommodating portion, magnetic particle suspension accommodating portion, tips accommodating portion, and reaction vessel or the like.

The fragmentation production area 60 includes a fragmentation area 60a and a production area 60b. The fragmentation area 60a has six cartridge containers 68, including the reaction vessel, arranged in parallel along the Y axis direction. The production area 60b is provided with six cartridge containers 69, including the magnetic particle suspension accommodating portion, arranged in parallel along the Y axis direction. Each of the wells or holes of the cartridge container 68 corresponds to the aforementioned fragmentation solution accommodating portion, reaction vessel, tips accommodating portion for accommodating the capillary electrophoresis tip, and electrophoresis solution accommodating portion. Each of the wells or holes of the cartridge container 69 corresponds to the binding promoter solution accommodating portion, dissociation solution accommodating portion, tips accommodating portion for accommodating the dispensing tip, and magnetic particle suspension accommodating portion. The cartridge container 68 also has a fluorescence labeling solution accommodating portion for labeling the fragments for molecular weight evaluation.

Similarly to the extraction area 50, a partition wall 17 is provided between the adjacent cartridge containers 68 and a partition wall 18 is provided between the adjacent cartridge containers 69.

The PCR area 70 is provided with six cartridge containers 75 arranged in parallel. Each of the wells or holes of the cartridge container 75 corresponds to the aforementioned amplification solution accommodating portion, sealing liquid accommodating portion, tips accommodating portion for accommodating the dispensing tip of a small capacity, and reaction vessel where PCR amplification can be performed. Also, a partition wall 19 is provided between the adjacent cartridge containers 75.

The sequencer pretreatment device 10 according to the present embodiment illustrated in FIG. 2 further includes, on the stage 15 thereof, six parent sample accommodating portions 57 for accommodating a parent sample taken from each patient, six final product accommodating portions 77, accommodating a finally generated product, to be transferred to a sequencer, and a tip accommodating portion 76 for accommodating the dispensing tip and the perforating tip.

The volume of the well of the cartridge containers 56, 68, 69, and 75 having been described above is, for example, approximately 200 μL while the reaction vessel is approximately 10 μL to 1 mL. The container 56 for accommodating a parent sample and containers 56 and 77 for accommodating a final product, etc. are approximately 2 mL.

In FIG. 2, each of the nozzles $41_1$ to $41_6$ of the nozzle head 40 is mounted with the dispensing tip 54 including a capillary 54a and a thick tube 54b on the side of the thick tube 54b. The nozzles $41_1$ to $41_6$ are arranged in a line shape on the nozzle array substrate 41. The upper side of the nozzle array substrate 41 has a cylinder housing portion provided with six cylinders as the suction and discharge mechanism 43. The inside of the cylinder is provided with a piston, a motor for driving the piston, and a ball screw rotatably attached by the motor. Reference sign 42 denotes a tip detaching plate, as a tip detaching unit 45, for detaching the dispensing tip 54 mounted to the nozzles $41_1$ to $41_6$ from the nozzles $41_1$ to $41_6$, having a U-shaped notched part larger than the diameter of the nozzles $41_1$ to $41_6$ and thinner than an outer diameter of the thickest portion of the tip. The tip detaching plate is driven by the motor driving the piston.

The nozzle head 40 is provided with a magnetic unit 44 having respective magnets 44a provided in such a manner as to allow for contact with and dissociation from the respective capillaries 54a such that magnetic force can be exerted to and removed from the capillaries 54a of the dispensing tip 54 mounted to the nozzles $41_1$ to $41_6$.

The magnetic unit 44, the suction and discharge mechanism 43, the tip detaching unit 45, and an electrode controller of the nozzle head 40 are provided to a head base movable in the X and Y axis directions. The nozzle array substrate 41 and a supporting member array board 42 are provided to a Z axis moving body movable in the Z axis direction relative to the head base.

The nozzle moving mechanism 80 has an X-axis moving mechanism and a Y-axis moving mechanisms, for allowing the head base to move in the X and Y axis directions and a Z-axis moving mechanism for moving the Z-axis movable body in the Z axis direction, relative to the accommodating portion group such as the extraction area 50 that corresponds to the container group and the absorbance measuring area 35, molecular weight evaluation area 36, and internal control measuring area 37 that correspond to the quality evaluation area.

The X-axis moving mechanism and Y-axis moving mechanism have, for example, an X-axis moving body movable in the X axis direction by a ball screw or the like driven to rotate by an X axis motor provided in connection with the stage and extending in the X axis direction and a Y axis moving body, coupled to the head base and the X-axis moving body, movably provided in the Y axis direction by a ball screw or the like, extending in the Y axis direction, and rotated by a Y axis motor provided in the X-axis moving body. The Z-axis moving body is provided coupled to a Z axis motor provided in the head base, a ball screw rotated by the Z-axis motor, and a nut unit screwed to the ball screw and rotated by rotation of the ball screw.

Figure 3:
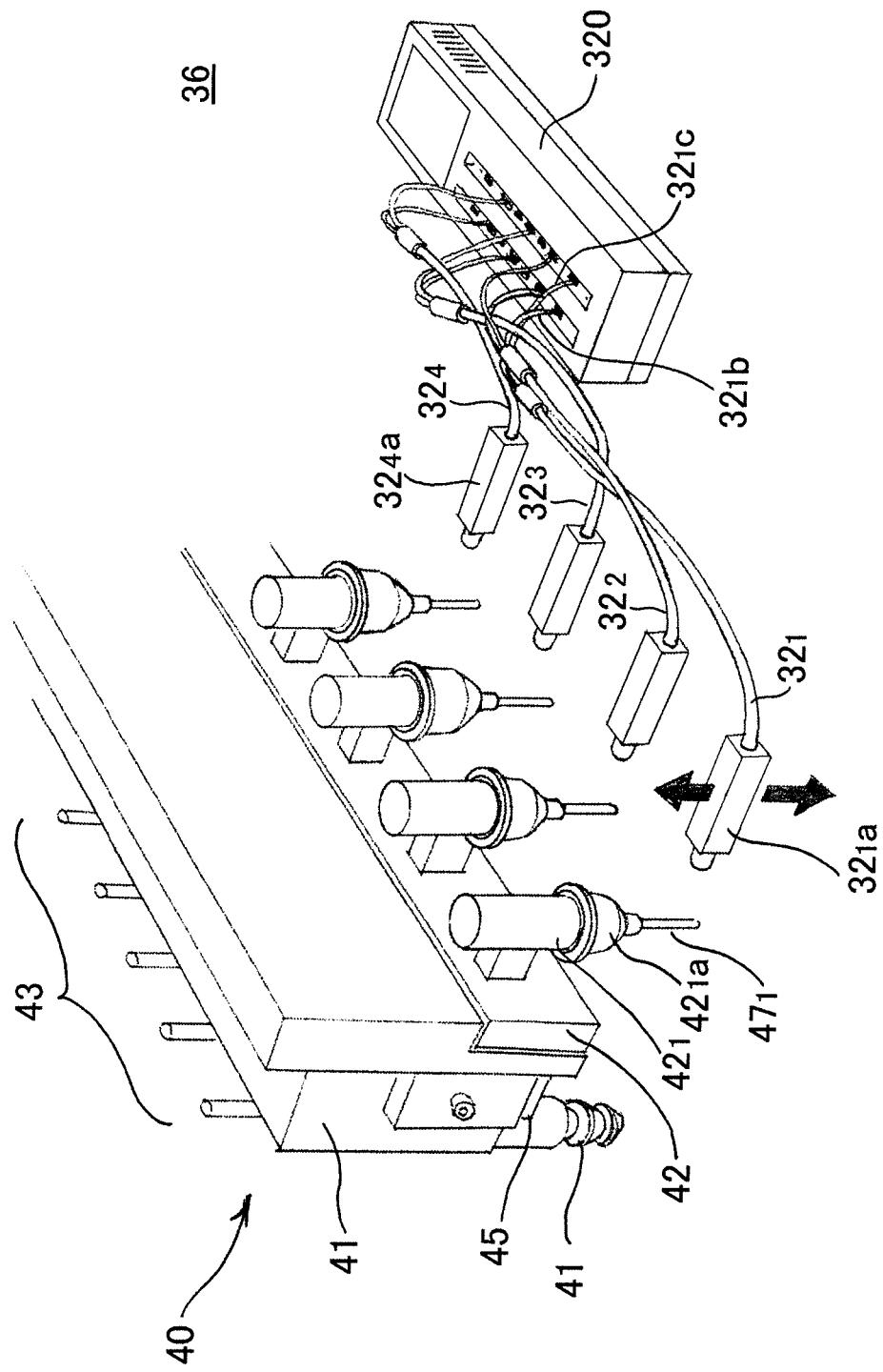
FIG. 3 is an enlarged partial perspective view illustrating parts of a nozzle head and an optical measuring instrument of the sequencer pretreatment device illustrated in FIG. 2.

FIG. 3 illustrates a nozzle array substrate 41 and a supporting member array board 42 of the nozzle head 40 according to an embodiment of the present invention. The respective nozzles $41_1$ to $41_6$ and the electrode supporting members $42_1$ to $42_6$ are arranged along the X axis direction in a line shape. Illustrated is the nozzle head 40 moved by the nozzle moving mechanism 80 such that the electrode supporting members $42_1$ to $42_6$ approach the measuring ends $32_1$a to $32_6$a of one end of the light guiding paths $32_1$ to $32_6$ in the molecular weight evaluation area 36. Reference sign $42_1$a denotes a cap, attached to the electrode supporting member $42_1$, having an electrode $47_1$ of a pin shape penetrating through the lower end thereof. Caps $42_1$a to $42_6$a are to be mounted with the capillary electrophoresis tip 64.

A plurality of one ends of the light guiding paths $32_1$ to $32_6$ are the measuring ends $32_1$a to $32_6$a attached to the electrode supporting member $42_1$, positioned in proximity of the capillary of the capillary electrophoresis tip 64, and provided movably along the Z axis direction. The light guiding paths $32_1$ to $32_6$ include two light guiding paths of light guiding paths $320_1$b to $320_6$b and $320_1$c to $320_6$c. Sets of the other two connecting ends of the respective light guiding paths are arranged in the connection end array body 320 at intervals shorter than predetermined intervals of the electrode supporting members $42_1$ to $42_6$ in a line shape. The light guiding path $320_1$b is for irradiating the capillary electrophoresis tip with a trigger for fluorescence excitation generated by the optical measuring instrument 31 while the light guiding path $320_1$c is for communicating fluorescence emitted from the inside of the capillary electrophoresis tip to a photo sensor incorporated in the optical measuring instrument 31 for conversion into an electric signal.

Figure 4:
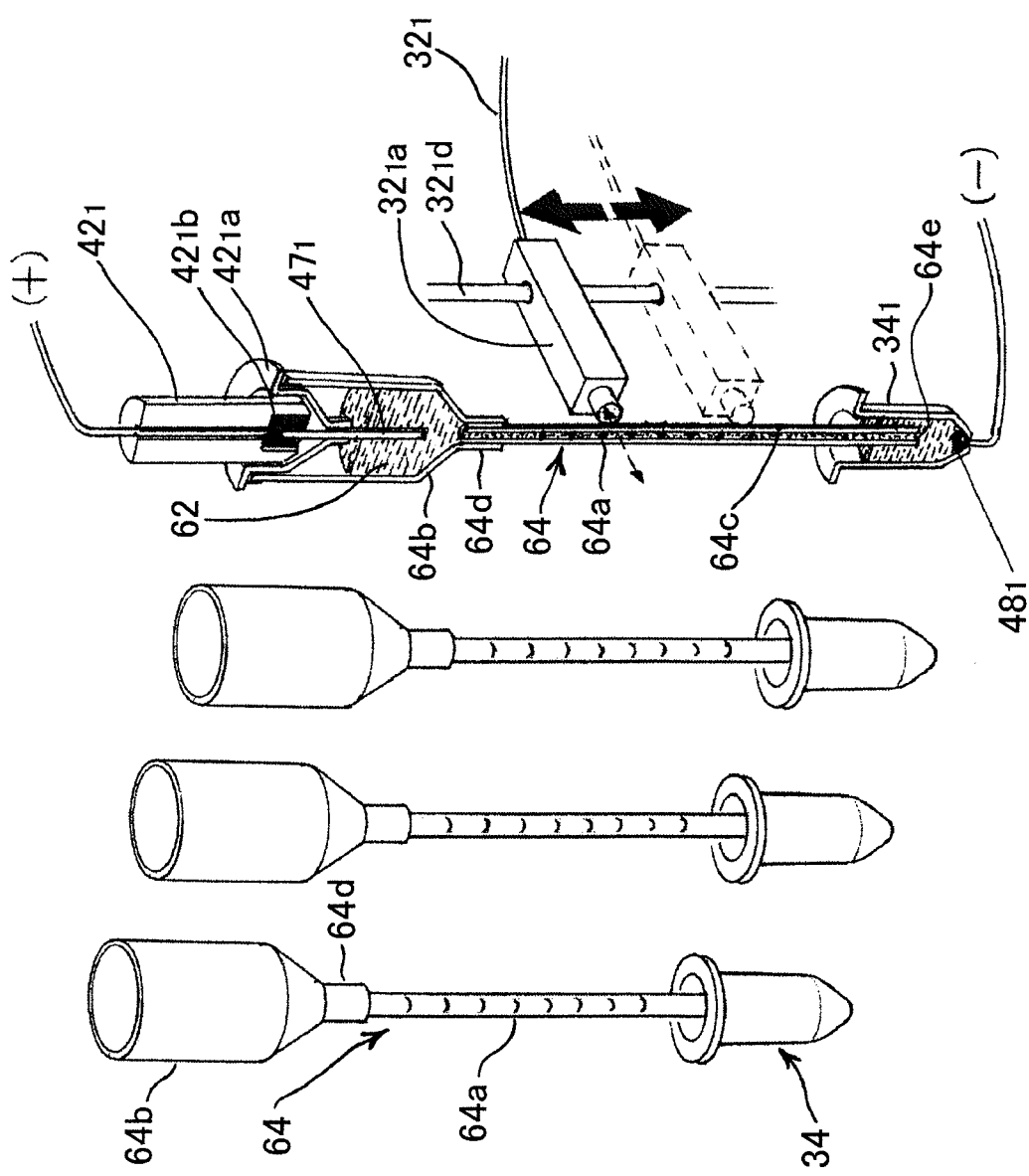
FIG. 4 is a partial cross-sectional perspective view illustrating a capillary electrophoresis tip and a use state thereof according to an embodiment of the present invention.

FIG. 4 illustrates the capillary electrophoresis tip 64 and the electrode supporting member according to an embodiment of the present invention.

The electrode supporting member $42_1$ is mounted with a cap $42_1$a at the tip portion thereof. The lower end of the cap $42_1$a is penetrated through by the first electrode $47_1$ of a pin shape. The first electrode $47_1$ is detachably attached to the electrode supporting member $42_1$ via an electrode combining terminal $42_1$b.

The capillary electrophoresis tip 64 includes a capillary 64a and a thick tube 64b communicated with the capillary 64a and formed thicker than the capillary 64a. The capillary 64a and the thick tube 64b are preferably formed as separate bodies with the upper end of the capillary 64a attached by being fitted to a fitting portion 64d in the lower end of the thick tube 64b. The inside of the capillary 64a is filled with agarose gel 64c for electrophoresis while the thick tube 64b accommodates, upon use, buffer solution which is electrophoresis solution 62. Target solution, namely, solution containing target fragment, is accommodated in the electrode-attached liquid accommodating portion $34_1$ while an opening 64e at the lower end of the capillary 64a is inserted into the electrode-attached liquid accommodating portion $34_1$. The first electrode $47_1$ is soaked into the electrophoresis solution 62 while the second electrode $48_1$ is soaked into the target solution. Thereafter, applying predetermined voltage between the first electrode $47_1$ and the second electrode $48_1$ allows electrophoresis to be performed.

Also, the measuring ends $32_1$a to $32_6$a of the electric light guiding paths $32_1$ to $32_6$ are provided to allow for movement in the vertical direction (Z axis direction) along guide shafts $32_1$d to $32_6$d along the capillary 64a. This allows the molecular weight of fragments contained in the target solution to be measured by measuring the position of the fragments labeled with fluorescence.

Figure 5:
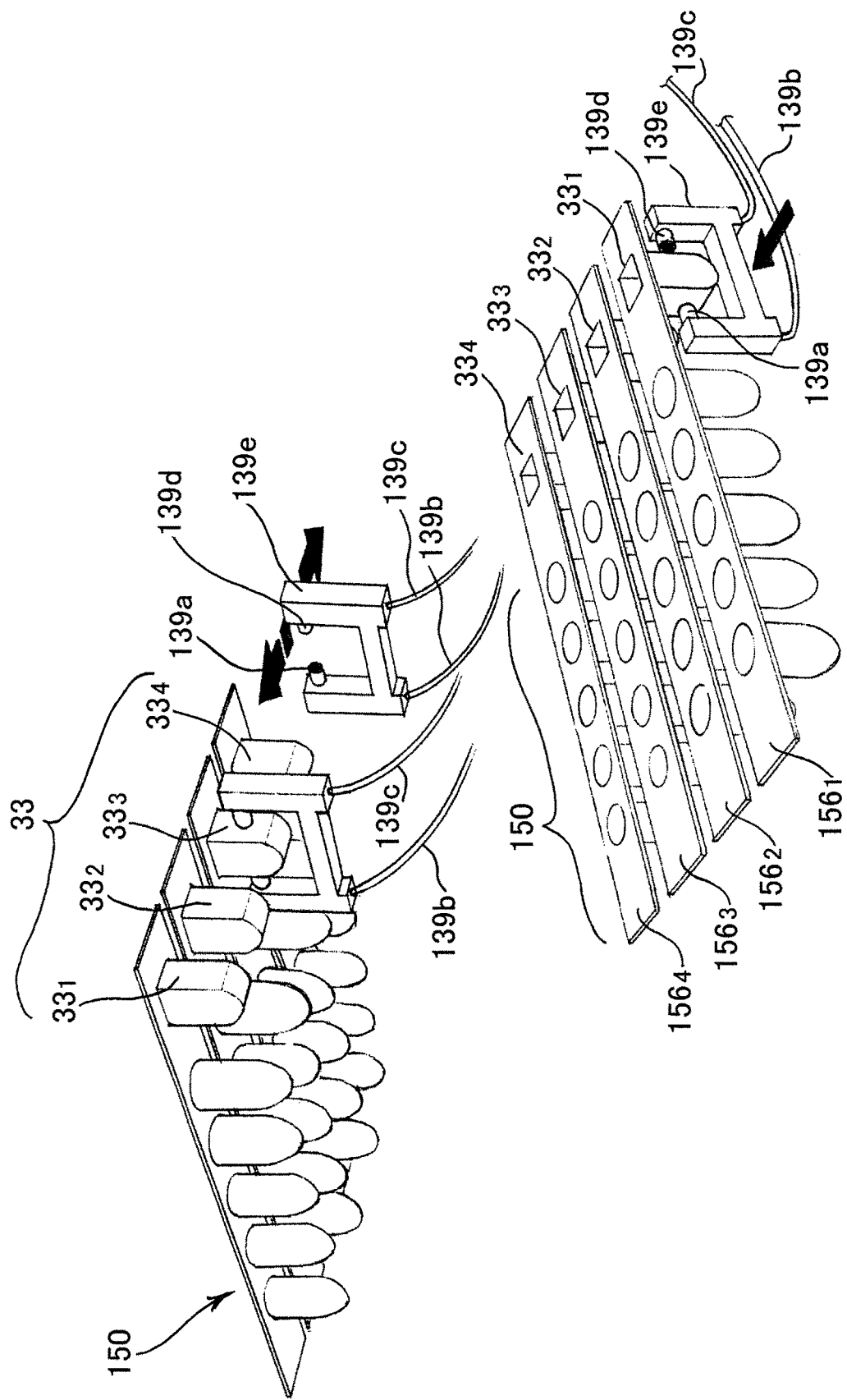
FIG. 5 is a perspective view illustrating a liquid accommodating portion and a part of an optical measuring instrument for absorbance measurement in FIG. 2 according to the embodiment of the present invention.

FIG. 5 illustrates an extraction area 150 according to an embodiment different from the extraction area 50 illustrated in FIG. 2. Unlike the movable optical measuring instrument 39, a fixed optical measuring instrument 139 is used. In a measuring end 139e, an irradiating end 139a at the tip of the light guiding paths 139b and 139c optically connected to an optical measuring instrument 139 and a light receiving end 139d are disposed at an interval in an opposing manner. The measuring end 139e moves such that a side surface of the translucent liquid accommodating portions $33_1$ to $33_6$ are arranged between the irradiating end and light receiving end.

The example of FIG. 5 differs from the case of FIG. 2 in that the liquid accommodating portions $33_1$ to $33_6$ are provided in the same cartridge containers $156_1$ to $156_6$ as respective sample accommodating portions $51_1$ to $51_6$ and $52_1$ to $52_6$ in the extraction area 150.

Figure 6:
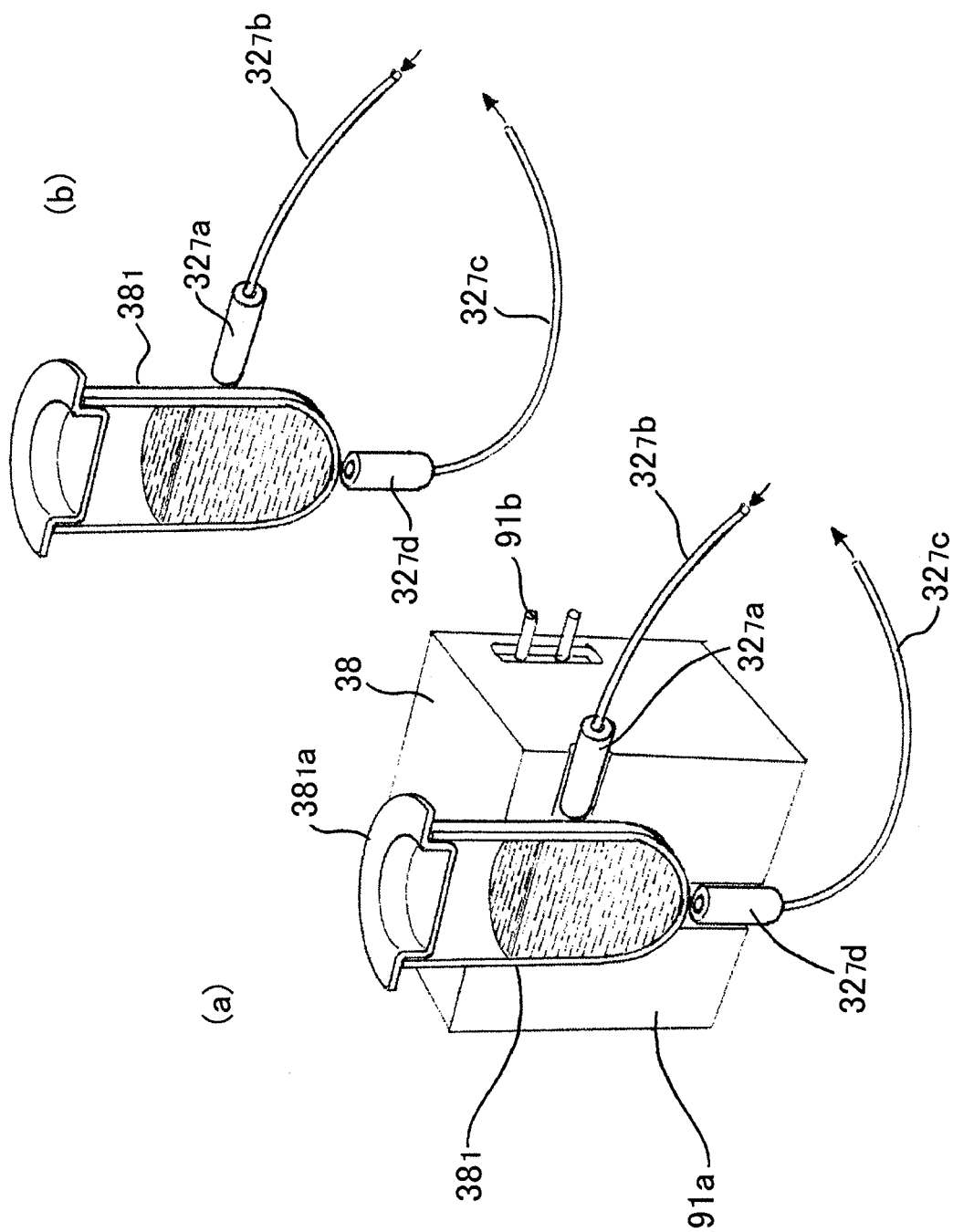
FIG. 6 is a cross-sectional view illustrating a PCR reaction vessel according to an embodiment of the present invention.

FIG. 6 illustrates an irradiating end $32_7$a and a light receiving end $32_7$d as measuring ends at the tip of the light guiding paths $32_7$ to $32_{12}$, and an irradiation light guiding path $32_7b$ and light receiving light guiding path $32_7c$ optically coupling the measuring ends with the optical measuring instrument 31 when the optical measuring instrument 31 measures fluorescence in the respective reaction vessels $38_1$ to $38_6$ in the internal control measuring area 37. FIG. 6(a) illustrates the array substrate 38 provided with a temperature control block 91a temperature of which is controlled by the temperature controller 91 while FIG. 6(b) illustrates when none of the temperature control block is provided. Sign $38_1a$ denotes a sealing lid for sealing the reaction vessels $38_1$ to $38_6$. Sign 91b denotes a lead wire for electrically connecting the temperature control block 91a to the temperature controller 91.

Next, the operation of the sequencer pretreatment device or the method according to an embodiment of the present invention will be described. A command given by a user by the operation unit 11 causes sample solution of diluted phlegm or the like, accommodated in six parent sample accommodating portions 57, sampled from six patients, and accommodated in the extraction area 50 among the container group to be accommodated in predetermined reaction vessels $55_1$ to $55_6$ in the extraction area 50 by mounting the dispensing tip 54, accommodated in the tips accommodating portions $54_1$ to $54_6$, to the nozzle of the nozzle head 40. After changing the dispensing tip, a predetermined amount of necessary reagent, for example approximately 0.5 to 1 mL for the magnetic particle suspension, is sequentially dispensed into the reaction vessels $55_1$ to $55_6$ from the extraction reagent accommodating portions $52_1$ to $52_6$ and magnetic particle suspension liquid accommodating portions $53_1$ to $53_6$, thereby allowing for reaction through mixing and stirring using the suction and discharge mechanism 43. This allows for destroying of cells to cause target nucleic acid to be dissolved into aqueous solution for capture by the magnetic particles. Next, by repeating suction and discharge while the magnetic unit exerts a magnetic field to the inside of the dispensing tip, thereby causing the magnetic particles to be adsorbed on the inner wall of the dispensing tip 54, removing the residual liquid, and performing suction and discharge of the dissociation solution while the magnetic unit 44 exerts a magnetic field to the inside of the dispensing tip 54, solution of nucleic acid is obtained for extraction of the nucleic acid. The above corresponds to an extraction step.

The obtained nucleic acid is, by moving the nozzle head 40 in the X axis direction while the nucleic acid is sucked into the dispensing tip 54, discharged into the reaction vessels $67_1$ to $67_6$ in the fragmentation production area 60.

In the reaction vessels $67_1$ to $67_6$, the fragmentation solution 61, accommodated in the fragmentation solution accommodating portions $61_1$ to $61_6$ in the fragmentation production area 60, is accommodated. Dispensing the solution containing the nucleic acid into the reaction vessels $67_1$ to $67_6$ and repeating suction and discharge together with the solution containing the nucleic acid using the dispensing tip 54 allow for reaction. The degree of fragmentation is dependent on the incubation time and the concentration of the fragmentation solution in the reaction vessels $67_1$ to $67_6$. Note that the temperature of incubation is at room temperature. The incubation is performed under atmospheric pressure. The incubation time (e.g. the order of "minute") and concentration of the fragmentation solution 61 are set depending on the degree of fragmentation a sequencer requires.

After the incubation time is completed, by moving the nozzle head 40 with the nozzles $41_1$ to $41_6$ mounted with the dispensing tip 54 in the Y axis direction, the magnetic particle suspension 63 having been sucked into the dispensing tip 54 is dispensed into the reaction vessels $67_1$ to $67_6$ accommodating the solution containing various fragments from the fragmented nucleic acid. After dispensing, repeating suction and discharge by the suction and discharge mechanism 43 causes the magnetic particles to be bound to and thus to capture the various fragments having been obtained as a result of fragmentation of the nucleic acid.

Then, repeating suction and discharge of solution, where the magnetic particles capturing the fragments are suspended, while a magnetic field is exerted to the inside of the dispensing tip 54, allowing the dispensing tip 54 to be moved to the reaction vessels $67_1$ to $67_6$ while the magnetic particles are adsorbed on the inner wall thereof, then removing the magnetic field from the inside of the dispensing tip 54, and repeating suction and discharge allow the magnetic particle suspension solution to be discharged and accommodated therein. Next, with the dispensing tip 54, a predetermined amount of the binding promoter solution 65 accommodated in the binding promoter solution accommodating portions $65_1$ to $65_6$ and the dissociation solution 66 accommodated in the dissociation solution accommodating portions $66_1$ to $66_6$ are dispensed into the reaction vessels $67_1$ to $67_6$ by causing the dispensing tip 54 to be moved in the Y axis direction using the nozzle head 40, thereby repeating suction and discharge to mix these solutions.

Figure 7:
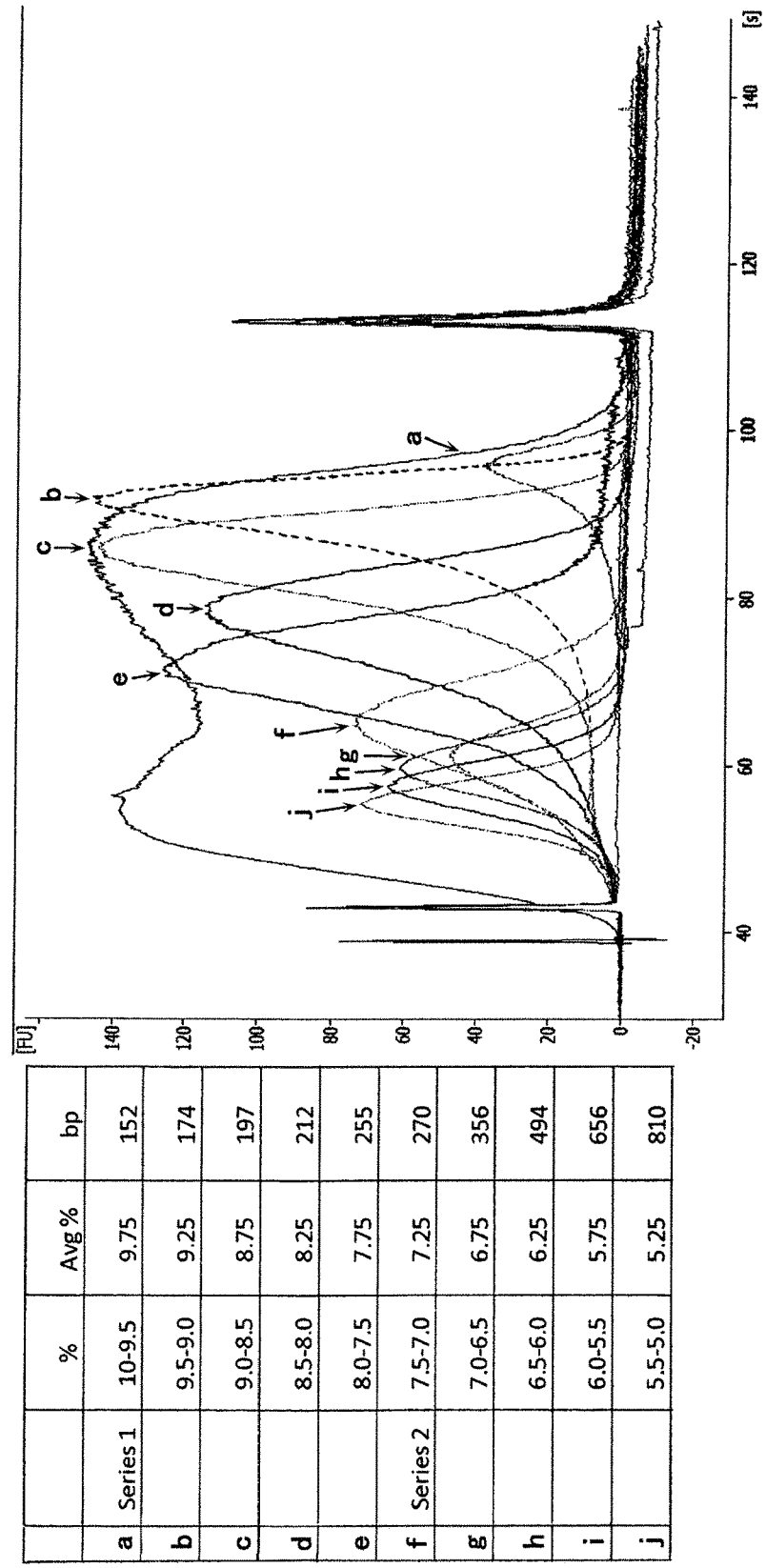
FIG. 7 includes a table and a graph of a test result illustrating contents of fragmentation control according to an embodiment of the present invention.

Then, as illustrated in a table on the left side of FIG. 7, when the average concentration of the binding promoter is, for example 9.75% of the entire solution, fragments having a molecular weight of 152 bp are dissociated from the magnetic particles and thus obtained. Similarly, when the average concentration of the binding promoter is lower, fragments having a larger molecular weight are gradually dissociated from the magnetic particles and thus obtained. From dispensing of the magnetic particle suspension to here corresponds to a selection step.

A graph on the right side illustrates experiment results where, with fragments labeled with fluorescence, the amount of fragments dissociated by electrophoresis was measured for ten different concentrations listed in the table (Series 1 illustrates a series of experiment results sequentially obtained by sequentially changing the amount of dissociation solution when a binding promoter concentration is 10 to 7.5% and recovering the dissociated fragments while Series 2 illustrates a series of experiment results, using different solution from that of Series 1, sequentially obtained by sequentially changing the amount of dissociation solution such that a binding promoter concentration becomes 7.5 to 5% and recovering the dissociated fragments). As illustrated in this graph, ten normal distributions corresponding to the order (a to j) of the ten concentrations listed in the table were obtained. Correspondence of the positions of the respective peaks (a to j) to the respective molecular weights, obtained by dissociation from the magnetic particles, listed in the table is clearly shown. Note that the horizontal axis of the graph represents the migration time, namely, migration distance, which corresponds to the size of the molecular weight.

Next, the dispensing tip 54 is removed from the nozzles $41_1$ to $41_6$ of the nozzle head 40 and a dispensing tip 73 of a small capacity is mounted instead. The dispensing tip 73 of a small capacity is mounted to the nozzle by causing the nozzle head 40 to be moved to the tips accommodating portions $73_1$ to $73_6$ in the PCR area 70 for descending in the Z axis direction. Including the selection step subsequent to the extraction step, the above corresponds to a fragmentation producing step.

Next, the nozzle head 40 is moved to the reaction vessels $67_1$ to $67_6$, where a predetermined amount of solution containing the produced fragments is accommodated, in the fragmentation production area 60. The solution containing the produced fragments is sucked for an amount that can be accommodated in the reaction vessels $74_1$ to $74_6$, for the PCR, having a capacity of 20 μL from the reaction vessels $67_1$ to $67_6$ and dispensed into the reaction vessels. Similarly, using the dispensing tip 73, the amplification solution is dispensed into the reaction vessels for mixing therein. The above corresponds to an amplification pretreatment step.

If the sequencer includes an amplification step of fragments, the obtained solution is the final product in the pretreatment and thus is accommodated in the final product accommodating portion 77. On the other hand, if the sequencer does not include the amplification step of fragments, a product obtained by the following amplification step is the final product. In the amplification step, with the dispensing tip 73, the sealing liquid is dispensed from the sealing liquid accommodating portions $72_1$ to $72_6$ into the reaction vessels $74_1$ to $74_6$ and then a predetermined temperature control required for amplification is performed by the temperature controller 91.

At least one of the respective steps may further includes a step of purifying nucleic acid or fragments thereof in such a manner as to meet a processing object of each of the steps by mixing, using the dispensing tip 54 mounted to the nozzles $41_1$ to $41_6$ of the sequencer pretreatment device 10, the product obtained as a result of the step with the magnetic particle suspension 53 and repeating suction and discharge of the mixed solution via the dispensing tip, thereby causing the magnetic particles to capture the nucleic acid or fragments thereof and to be adsorbed on the inner wall of the dispensing tip 54 with the magnetic unit 44.

Furthermore, as the quality evaluation step, in at least one of the respective steps, evaluation of the molecular weight of a product obtained as a result of the step may be performed using the sequencer pretreatment device.

For example, in the quality evaluation step, the fragmentation production area 60 has one or more capillary electrophoresis tips 64 including the capillary 64a sealed with agarose gel and a thick tube 64b communicating with the capillary 64a while the nozzle head 40 has one or more electrode supporting members $42_1$ to $42_6$, capable of supporting the capillary electrophoresis tip 64 on the side of the thick tube 64b upon mounting and provided with first electrodes $47_1$ to $47_6$, which are made movable relative to the fragmentation production area 60 of the container group together with the nozzles $41_1$ to $41_6$ by the nozzle moving mechanism 80.

Furthermore, the molecular weight evaluation area 36 of the quality evaluation area 30 of the container group has a plurality of (six in this example) electrode-attached liquid accommodating portions $34_1$ to $34_6$ having second electrodes $48_1$ to $48_6$ provided in such a manner to allow for contact with liquid to be accommodated. Upon a command from the operation unit 11, the nozzles $41_1$ to $41_6$ of the nozzle head 40 are mounted with the dispensing tip 54, thereby taking the solution containing the fragments to be evaluated on the molecular weight thereof from the reaction vessels $67_1$ to $67_6$ and dispensing into the electrode-attached liquid accommodating portions $34_1$ to $34_6$. An intercalator is dispensed into the solution for labeling the fragment with fluorescence.

Next, the electrophoresis solution 62 accommodated in the electrophoresis solution accommodating portions $62_1$ to $62_6$ of the fragmentation production area 60 is sucked with the dispensing tip 54 and the dispensing tip 54 is moved by the nozzle head 40 for dispensing into the thick tube 64b of the six capillary electrophoresis tip 64 accommodated in the tips accommodating portions $64_1$ to $64_6$.

Next, the nozzle head 40 is moved in the Y axis direction and thus the dispensing tip 54 is detached with tip detaching unit 45 at an empty accommodating portion of the tips accommodating portions $64_1$ to $64_6$. Thereafter, by moving the nozzle head 40 to be positioned over the capillary electrophoresis tip 64 and then causing the nozzle head to descend along the Z axis direction, the thick tube 64b of the capillary electrophoresis tip 64 is mounted and attached to the upper side of the caps $42_1$a to $42_6$a of the electrode supporting members $42_1$ to $42_6$, thereby allowing the electrodes $47_1$ to $47_6$ to be in contact with the electrophoresis solution 62.

The nozzle head 40 where the capillary electrophoresis tip 64 is mounted to the electrode supporting members $42_1$ to $42_6$ is moved to the molecular weight evaluation area 36. The opening 64e at the tip of the capillary 64a of the capillary electrophoresis tip 64 is then inserted into the solution in the electrode-attached liquid accommodating portion $34_1$ to $34_6$. In this state, predetermined voltage is applied between the first electrodes $47_1$ to $47_6$ and the second electrodes $48_1$ to $48_6$, thereby exerting an electric field to perform electrophoresis of the fragments. After a predetermined time, the measuring ends $32_1$a to $32_6$a are moved in the vertical direction along the capillary 64a for scanning, thereby measuring the fluorescence of the labeled fragments and determining the molecular weight of the fragments.

In this sequencer pretreatment device 10, the quality evaluation control unit 26 has an internal control measurement control unit for measuring the internal control fragment, having a specific base sequence inserted to a target fragment in the amplification step, labeled with labeled primers that binds with the base sequence. Furthermore, as for the target fragment, by not labeling or by labeling with the intercalator, the internal control measurement control unit performs measurement of amplification results on the internal control fragment and the target fragment.

Therefore, the solution containing the fragments produced using the magnetic particle suspension, from the solution having been obtained by the fragmentation of the target nucleic acid inserted with the internal control nucleic acid or a fragment thereof having a specific base sequence, is accommodated in the predetermined liquid accommodating portion in the fragmentation production area 60. The respective nozzles $41_1$ to $41_6$ of the nozzle head 40 are attached with the dispensing tip 73 of a small capacity and a predetermined amount (10 μL) of the solution containing the fragments is dispensed, from the liquid accommodating portion, into the reaction vessels $38_1$ to $38_6$ for PCR. Thereafter, the amplification solution 71, containing solution of a primer labeled in advance that can be bound with the specific base sequence of the internal control nucleic acid, is dispensed into the reaction vessels $38_1$ to $38_6$ to perform amplification by temperature control using the temperature controller 91.

Thereafter, the optical measuring instrument 31 is moved along the connection end array body 320 and irradiates with excitation light and receives fluorescence via the light guiding paths $32_7$ to $32_{12}$, thereby measuring the internal control fragment.

The sequencer pretreatment device 10 measures the concentration of the target nucleic acid by measuring the absorbance of the product obtained as a result of the extraction step by the quality evaluation control unit 26.

Upon a command from the operation unit 11, the nozzles $41_1$ to $41_6$ of the nozzle head 40 are mounted with the dispensing tip 54 from the tips accommodating portions $54_1$ to $54_6$ in the extraction area 50 and moved to the reaction vessels $55_1$ to $55_6$, thereby sucking a portion of the solution containing the extracted nucleic acid and dispensing into the translucent liquid accommodating portions $33_1$ to $33_6$ in the absorbance measuring area 35. Irradiating the solution accommodated in each of the liquid accommodating portions $33_1$ to $33_6$ with light of a particular wavelength, for example 260 nm, 280 nm, or from 200 nm to a wavelength within the range of visible light, or further light having a wavelength of 190 nm to 800 nm and measuring the absorbance allows the concentration of the fragments to be measured.

FIG. 5 illustrates where the irradiating end 139a and light receiving end 139d are disposed in an opposing manner and moved, thereby causing the liquid accommodating portions $33_1$ to $33_6$ to be sequentially arranged between the irradiating end 139a and light receiving end 139d for measurement. From data obtained through the light guiding paths 139b and 139c, the intensity of light transmitted by each of the liquid accommodating portions is measured by the optical measuring instrument 139 fixed to the stage, thereby measuring the absorbance.

Figure 8:
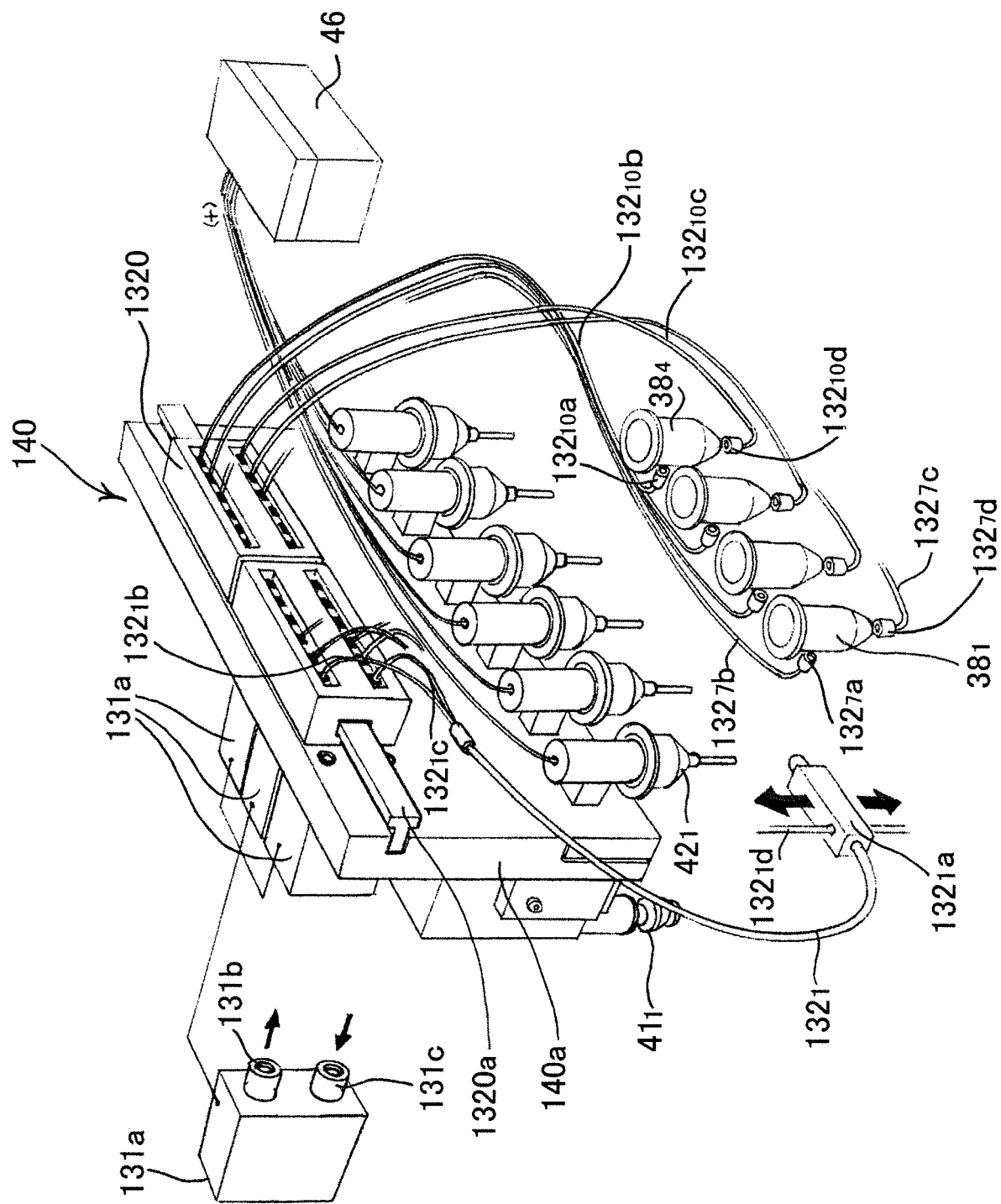
FIG. 8 is a perspective view illustrating a nozzle head and a portion of an optical measuring instrument according to another embodiment of the present invention.

FIG. 8 illustrates an optical measuring instrument 131a, corresponding to FIG. 3, according to another embodiment of the present invention. Three optical measuring instruments 131a corresponding to three types of fluorescence having different wavelengths are provided to the nozzle head 140 by being fixed thereto. The optical measuring instrument 131a has an emitting portion 131b for irradiating with excitation light and a light receiving end 131c for receiving fluorescence. Meanwhile, each of light guiding paths $132_1$ to $132_6$ has each of two light guiding paths $132_1b$ to $132_6b$ and $132_1c$ to $132_6c$ respectively for irradiation with excitation light and for receiving fluorescent light. A connection end array body 1320 is provided movably relative to the optical measuring instrument 131a such that a connection end of a rear end of each of the light guiding paths $132_1b$ to $132_6b$ for irradiation with excitation light is optically connectable with the emitting portion 131b while a connection end of a rear end of each of the light guiding paths $132_1c$ to $132_6c$ for receiving fluorescent light is optically connectable with the light receiving end 131c. Note that a tip (irradiating end) of each of the light guiding paths $132_1b$ to $132_6b$ for irradiation with excitation light and a tip (light receiving end) of each of the light guiding paths $132_1c$ to $132_6c$ for receiving fluorescent light are bundled as each of measuring ends $132_1a$ to $132_6a$ and provided movably in the vertical direction such that the measuring end approaches below each of the electrode supporting members. Furthermore, as for light guiding paths $132_7$ to $132_{12}$ of the connection end array body, tips (irradiating ends $132_7a$ to $132_{12}a$) of the respective light guiding paths $132_7b$ to $132_{12}b$ for irradiation are provided on side surfaces of the reaction vessels $38_1$ to $38_6$ while tips (light receiving ends $132_7d$ to $132_{12}d$) of the respective light guiding paths $132_7c$ to $132_{12}c$ for receiving light are provided in contact with bottom surfaces of the reaction vessels $38_1$ to $38_6$.

The above embodiments are specifically described for better understanding of the invention and are not intended to limit different forms. Therefore, there may be modifications within a range not changing the principals of the invention. For example, configurations, shapes, materials, arrangements, amount, and the number of items of the nozzle, dispensing tip, capillary electrophoresis tip, container group, accommodating portion group, quality evaluation area, optical measuring instrument, measuring end, suction and discharge mechanism, moving mechanism, magnetic unit, temperature controller, reaction vessel, sealing lid, sealing liquid, extraction reagent solution, fragmentation solution, binding promoter, magnetic particles, amplification solution, etc. and reagent, sample, etc. used are not limited to the examples shown in the embodiments. Moreover, it has been described that the nozzle is moved relative to the stage. However, the stage may be moved relative to the nozzle.

Furthermore, the component or components which form these components having been described in each of the embodiment of the present invention may be combined with each other with appropriate selection with appropriate changes.

INDUSTRIAL APPLICABILITY

The present invention relates to fields where, for example, processing, test, or analysis on nucleic acid primarily including DNA, RNA, mRNA, rRNA, and tRNA is required. For example, industrial field, agricultural fields such as food, agriculture, and seafood processing, chemical field, pharmaceutical field, medical fields such as sanitation, insurance, diseases, and genetics, and science fields such as biochemistry or biology. The present invention can be used especially for pretreatment for a large-scale sequencer.

REFERENCE SIGNS LIST 10 sequencer pretreatment device
20 CPU+program
30 quality evaluation area
31, 131 optical measuring instrument
$32_1$ to $32_{12}$, $132_1$ to $132_{12}$ light guiding path
$32_1b$ to $32_{12}b$, $132_1b$ to $132_{12}b$, $32_1c$ to $32_{12}c$, $132_1c$ to $132_{12}c$ light guiding path
35 absorbance measuring area
36 molecular weight evaluation area
37 internal control measuring area
40, 140 nozzle head
41 nozzle array substrate
$41_1$ to $41_6$ nozzle
42 electrode supporting member array board
$42_1$ to $42_6$ electrode supporting member
50, 150 extraction area
53, 63 magnetic particle suspension
54 dispensing tip
$55_1$ to $55_6$, $67_1$ to $67_6$, $74_1$ to $74_6$ reaction vessel
60 fragmentation production area
61 fragmentation solution
$61_1$ to $61_6$ fragmentation solution accommodating portion
64 capillary electrophoresis tip
65 binding promoter solution
$65_1$ to $65_6$ binding promoter solution accommodating portion
70 PCR area
73 small volume dispensing tip
90 accommodating portion group

The invention claimed is:

1. A sequencer pretreatment method using a sequencer pretreatment device comprising: a suction and discharge mechanism configured to suck and discharge gas; a nozzle head having one or more nozzles configured to detachably mount one or more dispensing tips communicated with the suction and discharge mechanism and capable of sucking and discharging liquid; a container group comprising at least a reaction vessel and a liquid accommodating portion for accommodating various liquids including a magnetic particle suspension; a moving mechanism configured to cause relative movement among the nozzle and the container group; and a magnetic unit capable of exerting a magnetic field to the inside of the dispensing tip mounted to the nozzle, the method comprising:
an extraction step of mixing a sample, an extraction reagent solution, and the magnetic particle suspension that is accommodated in the container group and extracting nucleic acid from the sample;
a fragmentation producing step of fragmenting the extracted nucleic acid by mixing the extracted nucleic acid with a fragmentation solution that is accommodated in the container group, mixing at least the fragmented nucleic acid with the magnetic particle suspension and a binding promoter that is accommodated in the container group, allowing the fragmented nucleic acid to bind with magnetic particles in the magnetic particle suspension, and producing, from the fragmented nucleic acid, fragments of the nucleic acid having a molecular weight within a predetermined range by adding a dissociation solution that is accommodated in the container group to the mixture of the fragmented nucleic acid, the magnetic particle suspension, and the binding promoter to obtain a desired concentration of the binding promoter based on a relationship between a concentration of the binding promoter and the molecular weight of the fragments to be produced, said relationship having been ascertained in advance by electrophoresis, and said dissociation solution causing the fragments having the molecular weight within the predetermined range to be dissociated from the magnetic particles in the magnetic particle suspension when the desired concentration of the binding promotor is obtained using the sequencer pretreatment device; and
an amplification pretreatment step of dispensing a predetermined volume of solution containing the produced fragments into the reaction vessel together with amplification solution using the sequencer pretreatment device.

2. The sequencer pretreatment method according to claim 1, wherein the sequencer pretreatment device further comprises a temperature controller capable of controlling the temperature in the reaction vessel, and wherein the method further comprises an amplification step of amplifying the produced fragments by controlling the temperature in the reaction vessel of the sequencer pretreatment device.

3. The sequencer pretreatment method according to claim 1, wherein the sequencer pretreatment device further comprises an optical measuring instrument configured to measure an optical state in various tips or the reaction vessel, and wherein the method further comprises a quality evaluation step.

4. The sequencer pretreatment method according to claim 1, further comprising a step of purifying the nucleic acid or the fragments thereof by mixing the nucleic acid or the fragments thereof with a predetermined magnetic particle suspension and repeating suction and discharge of the mixed solution via the dispensing tip mounted to the nozzle, thereby causing the magnetic particle suspension to capture the nucleic acid or the fragments thereof and to be adsorbed on the inner wall of the dispensing tip using the magnetic unit.

5. The sequencer pretreatment method according to claim 3, wherein the quality evaluation step comprises evaluating the molecular weight of the produced fragments using the sequencer pretreatment device.

6. The sequencer pretreatment method according to claim 3, wherein the quality evaluation step comprises evaluating the concentration of the nucleic acid or a fragment thereof using the sequencer pretreatment device.

7. The sequencer pretreatment method according to claim 5, wherein:
one or more capillary electrophoresis tips comprising a capillary and a thick tube, communicating with the capillary, sealed with gel, are accommodated in the container group;
the nozzle head has one or more electrode supporting members, which can support the capillary electrophoresis tip on the side of the thick tube, the one or more electrode supporting members are provided with a first electrode that may be in contact with an electrophoresis solution that is accommodated in the thick tube and are made movable relative to the container group together with the nozzle by the nozzle moving mechanism; and
the container group further comprises one or more electrode-attached liquid accommodating portions having a second electrode provided thereto in such a manner as to be in contact with liquid accommodated therein, wherein, in the quality evaluation step, evaluation of the molecular weight of the produced fragments is performed by dispensing the electrophoresis solution from the liquid accommodating portion provided to the container group for accommodating the electrophoresis solution into the thick tube, supporting the capillary electrophoresis tip by the electrode supporting member on the side of the thick tube and thereby allowing the electrophoresis solution to be in contact with the first electrode, dispensing the produced fragments into the electrode-attached liquid accommodating portion, labeling the produced fragments, and performing electrophoresis on the produced fragments by inserting a tip of the capillary into the electrode-attached liquid accommodating portion so that an electric field is exerted on the inside of the tip via the first and second electrodes, and measuring the inside of the capillary using the optical measuring instrument to evaluate the molecular weight of the produced fragments.

8. The sequencer pretreatment method according to claim 3, wherein the amplification step comprises an internal control measuring step of measuring an internal control nucleic acid or a fragment thereof using the sequencer pretreatment device as the quality evaluation step.

9. A sequencer pretreatment device comprising:
a suction and discharge mechanism configured to suck and discharge gas;
a nozzle head having one or more nozzles configured to detachably mount a dispensing tip communicated with the suction and discharge mechanism and capable of sucking and discharging liquid;
an extraction area container group comprising at least an extraction reaction vessel and liquid accommodating portions for accommodating various liquids including a magnetic particle suspension;
a fragmentation production area container group comprising at least a fragmentation reaction vessel and liquid accommodating portions for fragmenting extracted nucleic acid and producing fragmented nucleic acid;
a moving mechanism configured to cause relative movement among the nozzles, the extraction area container group and the fragmentation production area container group;
a magnetic unit positioned outside the dispensing tip mounted to the nozzle and configured to exert and remove a magnetic field inside the dispensing tip mounted to the nozzle; and
a control unit configured to control at least the suction and discharge mechanism, the moving mechanism, and the magnetic unit,
wherein the control unit comprises a processor and a program that, when executed by the processor, causes at least one of the suction and discharge mechanism, the moving mechanism, and the magnetic unit to:
mix a sample with an extraction reagent solution and the magnetic particle suspension that is accommodated in the extraction area container group and to extract nucleic acid from said mixture;
fragment the extracted nucleic acid by mixing the extracted nucleic acid with a fragmentation solution that is accommodated in the fragmentation production area container group, and to produce, from the fragmented nucleic acid, fragments of the nucleic acid having a molecular weight within a predetermined range; and
dispense a predetermined volume of a solution containing the produced fragments from the dispensing tip into the reaction vessel together with an amplification solution for mixing therewith,
wherein the program, when executed by the processor, causes the at least one of the suction and discharge mechanism, the moving mechanism, and the magnetic unit to produce the fragments having the molecular weight within the predetermined range by mixing at least the fragmented nucleic acid with the magnetic particle suspension and a binding promoter that is accommodated in the fragmentation production area container group so that the fragmented nucleic acid is allowed to bind with magnetic particles in the magnetic particle suspension, and producing the fragments having the molecular weight within the predetermined range by adding a dissociation solution that is accommodated in the fragmentation production area container group to the mixture of the fragmented nucleic acid, the magnetic particle suspension, and the binding promoter to obtain a desired concentration of the binding promoter based on a relationship between a concentration of the binding promoter and the molecular weight of the fragments to be produced, said relationship having been ascertained in advance by electrophoresis, and said dissociation solution causing the fragments having the molecular weight within the predetermined range to be dissociated from the magnetic particles in the magnetic particle suspension when the desired concentration of the binding promoter is obtained.

10. The sequencer pretreatment device according to claim 9, further comprising a temperature controller capable of controlling the temperature in the fragmentation reaction vessel,
wherein the program, when executed by the processor, causes the temperature controller to amplify the produced fragments by controlling the temperature in the fragmentation reaction vessel.

11. The sequencer pretreatment device according to claim 9, further comprising an optical measuring instrument configured to measure an optical state in the various tips or the fragmentation reaction vessel, wherein the program, when executed by the processor, causes the optical measuring instrument to perform quality evaluation of the produced fragments.

12. The sequencer pretreatment device according to claim 9, wherein the program, when executed by the processor, causes at least one of the suction and discharge mechanism, the moving mechanism, and the magnetic unit to purify the nucleic acid or a fragment thereof by mixing and stirring solution containing the nucleic acid or a fragment thereof with the magnetic particle suspension by sucking and discharging, allowing the magnetic particle to capture the target nucleic acid or a fragment thereof, exerting a magnetic field to the inside of the dispensing tip and thereby allowing the capturing magnetic particle to be adsorbed on the inner wall thereof.

13. The sequencer pretreatment device according to claim 9, wherein:
one or more capillary electrophoresis tips comprising a translucent capillary and a thick tube, communicating with the capillary, sealed with gel, are accommodated in the fragmentation container group;
the nozzle head has one or more electrode supporting members, which can support the capillary electrophoresis tip on the side of the thick tube, the one or more electrode supporting members are provided with a first electrode that may be in contact with an electrophoresis solution that is accommodated in the thick tube and are made movable relative to the fragmentation container group together with the nozzle by the moving mechanism; and
the fragmentation container group further comprises one or more electrode-attached liquid accommodating portions having a second electrode provided thereto that may be in contact with liquid accommodated therein.

14. The sequencer pretreatment device according to claim 11, wherein:
the optical measuring instrument is provided such that the absorbance of the inside of one or more translucent liquid accommodating portions provided to the fragmentation container group can be measured; and
a solution containing the produced fragments is accommodated in each of the liquid accommodating portions; and
the program, when executed by the processor, causes the optical measuring instrument to measure the absorbance of each of the liquid accommodating portions.

15. The sequencer pretreatment device according to claim 13, wherein the program, when executed by the processor, causes at least one of the suction and discharge mechanism, the moving mechanism, and the magnetic unit to evaluate the molecular weight of the produced fragments by dispensing the electrophoresis solution from the liquid accommodating portion provided to the fragmentation container group for accommodating the electrophoresis solution into the thick tube, supporting the capillary electrophoresis tip by the electrode supporting member on the side of the thick tube and thereby allowing the solution to be in contact with the first electrode, dispensing the produced fragments into the electrode-attached liquid accommodating portion, labeling the produced fragments, and performing electrophoresis on the produced fragments by inserting a tip of the capillary into the electrode-attached liquid accommodating portion so that an electric field is exerted on the inside of the tip via the first and second electrodes, and measuring the inside of the capillary using the optical measuring instrument to evaluate the molecular weight of the produced fragments.

16. The sequencer pretreatment device according to claim 13, wherein the first electrode is mounted to an electrode mounting portion of the electrode supporting member in an electrically conductive manner.

17. The sequencer pretreatment device according to claim 13, wherein:
   the electrode supporting member comprises a cap covering a tip of the electrode supporting member;
   the first electrode of the electrode supporting member projects from the cap by penetrating therethrough; and
   the capillary electrophoresis tip is attached to the cap, thereby sealing an opening of the tip.

18. The sequencer pretreatment device according to claim 13, further comprising:
   one or more flexible light guiding paths, each having a front end and a rear end, the front end provided in proximity to or in contact with the capillary of one or more capillary electrophoresis tips and along the capillary in a movable manner, or in proximity to or in contact with a side surface of one or more translucent reaction vessels;
   an array body where the rear ends are arranged along a predetermined path; and
   the optical measuring instrument configured to be sequentially connectable to the rear end in an optical manner and to be relatively movable along the predetermined path of the array body.

* * * * *